United States Patent
Bujard et al.

(10) Patent No.: US 9,181,556 B2
(45) Date of Patent: Nov. 10, 2015

(54) TETRACYCLINE INDUCIBLE TRANSCRIPTION CONTROL SEQUENCE

(75) Inventors: Hermann Bujard, Heidelberg (DE); Rainer Loew, Frankfurt (DE)

(73) Assignee: TET SYSTEMS GMBH & CO., KG, Heidelberg (DE)

( * ) Notice: Subject to any disclaimer, the term of this patent is extended or adjusted under 35 U.S.C. 154(b) by 280 days.

(21) Appl. No.: 13/121,673

(22) PCT Filed: Aug. 19, 2009

(86) PCT No.: PCT/EP2009/060728
§ 371 (c)(1),
(2), (4) Date: May 31, 2011

(87) PCT Pub. No.: WO2010/037593
PCT Pub. Date: Apr. 8, 2010

(65) Prior Publication Data
US 2011/0247088 A1 Oct. 6, 2011

(51) Int. Cl.
*C07H 21/04* (2006.01)
*C12N 15/63* (2006.01)
*A61K 31/70* (2006.01)

(52) U.S. Cl.
CPC .... *C12N 15/635* (2013.01); *C12N 2770/40043* (2013.01); *C12N 2830/003* (2013.01)

(58) Field of Classification Search
CPC .................. C12N 15/635; C12N 2770/40043; C12N 2830/003
USPC .......................................... 536/24.1; 435/455
See application file for complete search history.

(56) References Cited

U.S. PATENT DOCUMENTS

| | | | |
|---|---|---|---|
| 4,736,866 A | 4/1988 | Leder et al. | |
| 4,870,009 A | 9/1989 | Evans et al. | |
| 5,464,758 A | 11/1995 | Gossen et al. | |
| 5,654,168 A | 8/1997 | Bujard et al. | |
| 5,789,156 A | 8/1998 | Bujard et al. | |
| 5,814,618 A | 9/1998 | Bujard et al. | |
| 5,854,310 A | 12/1998 | Maxson | |
| 5,866,755 A | 2/1999 | Bujard et al. | |
| 5,888,981 A | 3/1999 | Bujard et al. | |
| 5,891,665 A * | 4/1999 | Wilson | 435/69.1 |
| 5,912,411 A | 6/1999 | Bujard et al. | |
| 6,004,941 A | 12/1999 | Bujard et al. | |
| 6,087,166 A | 7/2000 | Baron et al. | |
| 6,136,954 A | 10/2000 | Bujard et al. | |
| 6,242,667 B1 | 6/2001 | Bujard et al. | |
| 6,252,136 B1 | 6/2001 | Bujard et al. | |
| 6,271,341 B1 | 8/2001 | Baron et al. | |
| 6,271,348 B1 | 8/2001 | Bujard et al. | |
| 6,914,124 B2 | 7/2005 | Bujard et al. | |
| 7,541,446 B2 | 6/2009 | Hillen et al. | |
| 2003/0221203 A1 | 11/2003 | Siamak | |
| 2010/0003686 A1 | 1/2010 | Shibahara et al. | |
| 2010/0310521 A1 * | 12/2010 | Fechner et al. | 424/93.6 |

FOREIGN PATENT DOCUMENTS

| | | |
|---|---|---|
| WO | WO 96/01313 | 1/1996 |
| WO | WO 00/75347 A2 | 12/2000 |
| WO | WO 2006/028480 A1 | 3/2006 |
| WO | WO 2007/133797 A2 | 11/2007 |
| WO | WO 2007/133798 A2 | 11/2007 |
| WO | WO2008/050774 * | 2/2008 |

OTHER PUBLICATIONS

Miwa et al Duplicated CArG Box domains have positive and mutally dependent regulatory roles in expression of the human alpha-cardiac actin gene. Molecular and Cellular Biology 7:2803-2813, 1987.*
Evans et al. Activator-mediated disruption of sequence-specific DNA contacts by the general transcription factor TFIIB. Genes & Development 15:2945-2949, 2001.*
Bink et al. The 5'-Proximal hairpin of Turnip Yellow Mosaic Virus RNA: Its role in translation and encapsidation. J. Virol. 77:7452-7458, 2003.*
Loew et al. Improved Tet-responsive promoters with minimized background expression. BMC Biotechnology 10:1-13, 2010.*
Agha-Mohammadi et al., "Second-generation tetracycline-regulatable promoter: repositioned tet operator elements optimize transactivator synergy while shorter minimal promoter offers tight basal leakiness," *The Journ. of Gene Med.*, pp. 817-828 (2004).
Baubonis et al., "Genomic targeting with purified Cre recombinase," *Nucleic Acids Res.*, vol. 21, No. 9, pp. 2025-2029 (1993).
Becker et al., "New plant binary vectors with selectable markers located proximal to the left T-DNA border," *Plant Molecular Biology*, vol. 20, pp. 1195-1197 (1992).
Belikov et al., "Nuclear Factor 1 and Octamer Transcription Factor 1 Binding Preset the Chromatin Structure of the Mouse Mammary Tumor Virus Promoter for Hormone Induction," *The Journ. of Biological Chemistry*, vol. 279, No. 48, pp. 49857-49867, (2004).
Bevan, "Binary Agrobacterium vectors for plant transformation," vol. 12, No. 22, pp. 8711-8721 (1984).

(Continued)

*Primary Examiner* — Quang Nguyen
(74) *Attorney, Agent, or Firm* — Foley & Lardner LLP

(57) ABSTRACT

The present invention relates to inducible transcription control sequences for the regulation of gene expression. Specifically, it relates to an transcription control sequence comprising at least two tet operator sequence motifs allowing the binding of tetracycline-dependent transcriptional regulators, wherein each of the tetracycline-dependent transcriptional regulators binds with respect to its neighbor to an opposite face of the DNA helix, and a minimal promoter comprising a TATA box which is linked at its 5' end to a general transcription factor binding site. Further, the present invention relates to a vector, a host cell, a plant or a non-human transgenic animal comprising the transcription control sequence. Also contemplated is a method for regulating the expression of a nucleic acid sequence being operatively linked to the transcription control sequence of the present invention in a host cell, a plant or a non-human transgenic animal.

12 Claims, 7 Drawing Sheets

(56) References Cited

OTHER PUBLICATIONS

Figure 2:
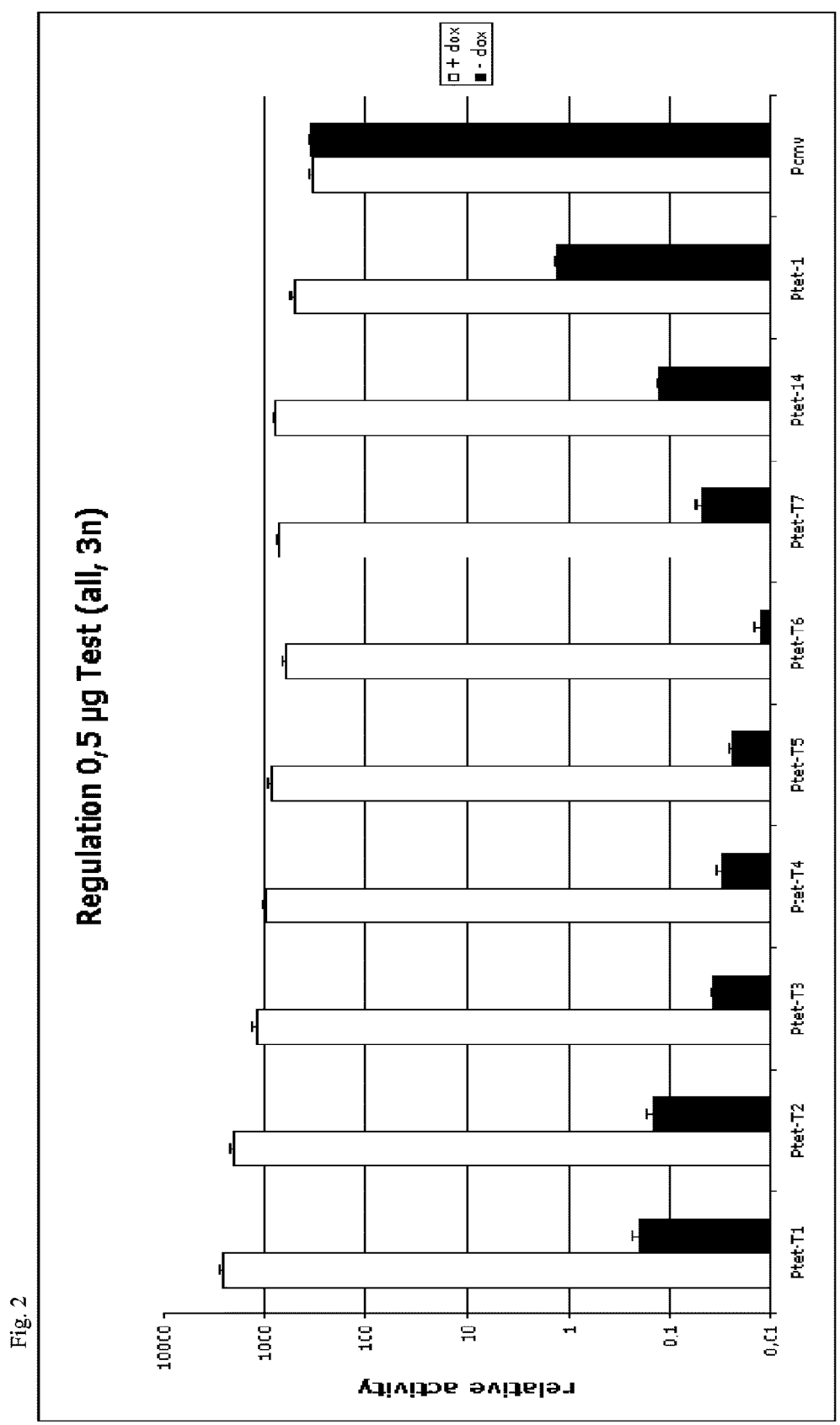

Bonin et al., "Photinus pyralis luciferase: vectors that contain a modified luc coding sequence allowing convenient transfer into other systems," *Gene*, vol. 141, pp. 75-77 (1994).

Cato et al., "mineralocorticoid Regulation of Transcription of Transfected Mouse Mammary Tumor Virus DNA in Cultured Kidney Cell," *The Journ. Cell Biol.*, vol. 106, pp. 2119-2125 (1988).

Dang et al., "Use of a Yeast Site-Specific Recombinase to Generate Embryonic Mosaics in Drosophila," *Developmental Genetics*, vol. 13, pp. 367-375 (1992).

Fiering et al., "An "in-out" strategy using gene targeting and FLP recombinase for the functional dissection of complex DNA regulatory elements: Analysis of the B-globin locus control region," *Proc. Natl. Acad. Sci.*, vol. 90, pp. 8469-8473 (1993).

Fukushige et al., "Genomic targeting with a positive-selection *lox*, integration vector allows highly reproducible gene expression in mammalian cells," *Proc. Natl. Acad. Sci*, vol. 89, pp. 7905-7909 (1992).

Ghazal et al., "Enhancement of RNA Polymerase II Initiation Complexes by a Novel DNA Control Domain Downstream from the Cap Site of the Cytomegalovirus Major Immediate-Early Promoter," *Journ. of Virology*, pp. 2299-2307 (1991).

Gossen et al., "Tight control of gene expression in mammalian cells by tetracycline-responsive promoters," *Proc. Natl. Acad. Sci.*, vol. 89, pp. 5547-5551 (1992).

Hillen et al., "Nucleotide sequence of the Tn10 encoded tetracycline resistance gene," vol. 11, No. 2. *Nucleic Acids Res.*, pp. 525-539 (1983).

Hoffmann et al., "A novel tetracycline-dependent expression vector with low basal expression and potent regulatory properties in various mammalian cell lines," *Nucleic Acids Res.*, vol. 25, No. 5, pp. 1078-1079 (1997).

Holmqvist et al., "FoxA1 binding to the MMTV LTR modulates chromatin structure and transcription," *Exper. Cell Res.*, vol. 304, pp. 593-603 (2005).

Li et al., "Targeted Mutation of the DNA Methyltransferase Gene Results in Embryonic Lethality," *Cell*, vol. 69, pp. 915-926 (1992).

Loew et al., "Retroviral vectors containing Tet-controlled bidirectional transcription units for simultaneous regulation of two gene activities," *Journ. of Molecular and Genetic Medicine*, vol. 2, No. 1, pp. 107-118 (2006).

Matys et al., "TRANSFAC: transcriptional regulation, from patterns to profiles," *Nucleic Acids Research*, vol. 31, No. 1, pp. 374-378 (2003).

Potle et al., "Nucleotide sequence of the repressor gene of the TN10 tetracycline resistance determinant," vol. 12, No. 2, pp. 4849-4863 (1984).

Stieger et al., "In vivo gene regulation using tetracycline-regulatable systems," *Advanced Drug Delivery Reviews* 61, pp. 527-541 (2009).

Thomas et al., "Site-Directed Mutagenesis by Gene Targeting in Mouse Embryo-Derived Stem Cells," *Cell*, vol. 51, pp, 503-512 (1987).

Tovar et al., "Identification and nucleotide sequence at the class E *tet* regulatory elements and operator and inducer binding of the encoded purified Tet repressor," *Mol. Gen. Genet.*, vol. 215, pp. 76-80 (1988).

Ueberham et al., "Conditional Tetracycline-Regulated Expression of TGF-B1 in Liver of Transgenic Mice Leads to Reversible Intermediary Fibrosis," *Hepatology*, pp. 1067-1078 (2003).

Unger et al., "Nucleotide sequence of the gene, protein purification and characterization of the pSC101-encoded tetracycline resistance-gene-repressor," *Gene*, pp. 103-108 (1984).

Unger et al., "Nucleotide sequence of the repressor gene of the RA1 tetracycline resistance determinant: structural and functional comparison with three related Tet repressor genes," vol. 12, No. 20, pp. 7693-7703 (1984).

Vigna et al., "Robust and Efficient Regulation of Transgene Expression in Vivo by Improved Tetracycline-Dependent Lentiviral Vectors," *Molecular Therapy*, vol. 5, No. 3, pp. 252-261 (2002).

Waters et al., "The tetracycline resistance determination of RP1 and Tn1721: nucleotide sequence analysis," vol. 11, No. 17, pp. 6089-6105 (1983).

Weidenfeld et al., "Inducible expression of coding and inhibitory RNAs from retargetable genomic loci," *Nucleic Acids Res.*, pp. 1-11 (2009).

Xu et al., "Cloning in a plasmid of an MMTV from a wild Chinese mouse: sequencing of the viral LTR," *Virus Research*, pp. 167-178 (1994).

Backman et al., "Tetracycline-inducible expression systems for the generation of transgenic animals; a comparison of various inducible systems carried in a single vector," *Journ. of Neuroscience Methods*, vol. 139, pp. 257-262 (2004).

\* cited by examiner

Fig.1

P_et-T minimal promoter series:

```
        Hin dIII                      TFIIB    TATA              +1  initiator
T1  AACCTTGCTAGCCTGTACCCTCCCAGGCCtatataaCAGAACCTCGTTTACTGAACCGtcagatcgcctgGAGACCCCATCCAC
T2  AAGCTTGGTAGGCGTGTACGGTGTGGGTgggCgcctataAaaGCAGAGCTCGTTTAGTGAACCGtcagatcgcctgGAGACGCCATCCAC
T3  AAGCTT--TAGGCGTGTACGGTgggC-gcctataAaaGCAGAGCTCGTTTAGTGAACCGtcagatcgcctgGAGACGCCATCCAC
T4  AAGCTT--TAGGCGTGTACGGTgggC-gcctataAaaGCAGAGCTCGTTTAGTGAACCGtcagatcgcctgGAGAgtcgacacca-g
T5  AAGCTT--TAGGCGTGTACGGTgggC-gcctataAaaGCAGAGCTCGTTTAGTGAACCGtcagatcgcctgGAGgtaatcaacta
T6  AAGCTT--TAGGCGTGTACGGTgggC-gcctataAaaGCAGAGCTCGTTTAGTGAACCGtcagatcgcctgGAG---------
T7  AAGCTT--TAGGCGTGTACGGTgggC-gcctataAaaGCAGAGCTCGTTTAGTGAACCGtcagatcgcctgGAGCtaatcaacta Sal I      Nco I
T1  GCTGTTTTGACCTCCATAGAGACACCGGGACCGATCCAGCTCCGCGCCTCCGCGgtcgacaccatgg  (58)
T2  GCTGTTTTGACCTCCATAGAAGACACCGGGACCGATCCAGCTCCAGCCCGCGCCGgtcgacaccatgg  (59)
T3  GCTGTTT-----CCATAGAAGAgtcgacaccatgg  (60)
T4  g  (61)
T5  ccaattccagctctctttgacaactgtcttataccaactttccgtaccacttCCTaccctcctaagacaattgcaagtcgacaccatgg  (62)
T6  --aattccaCAAcActtttg------tcttataccaactttccgtaccacttCCTaccctcgTaaagtcgacaccatgg  (63)
T7  ccaattccagctctctttgacaactgtcttataccaactttccgtaccacttCCTaccctcCtaagacaattgcaaagtcgacaccatgg  (64)
```

Fig. 4

A:

```
                                                      GAATTCTTTACT
CCCTATCAGTGATAGAGAAtGTATGAAGAGTTTACTCCCTATCAGTGATA
GAGAAtGTATGCAGACTTTACTCCCTATCAGTGATAGAGAAtGTATAAGG
AGTTTACTCCCTATCAGTGATAGAGAAtGTATGACCAGTTTACTCCCTAT
CAGTGATAGAGAAtGTATCTACAGTTTACTCCCTATCAGTGATAGAGAAt
GTATATCCAGTTTACTCCCTATCAGTGATAGAGAAtGTATAAGCTTTAGG
                          ←44bp----------------
---------------→
CaTGTACaGTGGGCaCCTATAAAAGCAGAGCTCaTTTAGTGAACtGTCAG
AttGCCTGGAGCAATTCCACAACACTTTTGTCTTATACCAACTTTCCaTA
CCACTTCCTACCCTCaTAAAGTgcACACCATGG
```

B:

```
CCATGGTGTGCACTTTATGAGGGTAGGAAGTGGTATGGAAAGTTGGTATA
AGACAAAAGTGTTGTGGAATTGCTCCAGGCAATCTGACAGTTCACTAAAT
GAGCTCTGCTTTTATAGGTGCCCACTGTACATGCCTAAGAATTCTTTACT
          ←44bp--------------------------
-------→
CCCTATCAGTGATAGAGAATGTATGAAGAGTTTACTCCCTATCAGTGATA
GAGAATGTATGCAGACTTTACTCCCTATCAGTGATAGAGAATGTATAAGG
AGTTTACTCCCTATCAGTGATAGAGAATGTATGACCAGTTTACTCCCTAT
CAGTGATAGAGAATGTATCTACAGTTTACTCCCTATCAGTGATAGAGAAT
GTATATCCAGTTTACTCCCTATCAGTGATAGAGAATGTATAAGCTTTAGG
                          ←44bp----------------
---------------→
CATGTACAGTGGGCACCTATAAAAGCAGAGCTCATTTAGTGAACTGTCAG
ATTGCCTGGAGCAATTCCACAACACTTTTGTCTTATACCAACTTTCCATA
CCACTTCCTACCCTCATAAAGTGCACACCATGG
```

FIG. 4 Continued

| SEQ ID NO: | sequence |
|---|---|
| 1 | 5'- tccctatcaGtgatagaga |
| 2 | 5'- GGTAGGCGTGTACGGTGGGAGGCCTATATAAGCAGAGCTCGTTTAG TGAACCGtCAGATCGCCTGGAGACGCCATCCACGCTGTTTTGACCTCCAT AGAAGACACCGGGACCGATCCAGCCTCCGCGG |
| 3 | 5'- gggcgcc |
| 4 | 5'- tataaaa |
| 5 | 5'- GGTAGGCGTGTACGGTGGGCGCCTATAAAAGCAGAGCTCGTTTAGT GAACCGtCAGATCGCCTGGAGACGCCATCCACGCTGTTTTGACCTCCATA GAAGACACCGGGACCGATCCAGCCTCCGCG |
| 6 | 5'- ccgtaaccacttGCAAccc |
| 7 | 5'- tcCAGCtctc |
| 8 | 5'- cagctctcttttgacaactg |
| 9 | 5'- caaccctcgtaagacaattgcaaa |
| 10 | 5'- TAGGCGTGTACGGTGGGCGCCTATAAAAGCAGAGCTCGTTTAGTGA ACCGtCAGATCGCCTGGAGA |
| 11 | 5'- gtaatcaactaccaattcCAGCtctcttttgacaactggtcttata ccaactttccgtaccacttGCAAcctcgtaagacaattgcaa |
| 12 | 5'- aattccacaacacttttgtcttataccaactttccgtaccacttcc taccctcgtaaa |
| 13 | 5'- tttactccctatcagtgatagagaacgtatgaagagtttactccct atcagtgatagagaacgtatgcagactttactccctatcagtgatagaga acgtataaggagtttactccctatcagtgatagagaacgtatgaccagtt tactccctatcagtgatagagaacgtatctacagtttactccctatcagt gatagagaacgtatatccagtttactccctatcagtgatagagaacgtat aagctttaggcgtgtacggtgggcgcctataaaagcagagctcgtttagt gaaccgtcagatcgcctggagacgccatccacgctgtttccatagaaga |
| 14 | 5'- tttactccctatcagtgatagagaacgtatgaagagtttactccct atcagtgatagagaacgtatgcagactttactccctatcagtgatagaga acgtataaggagtttactccctatcagtgatagagaacgtatgaccagtt tactccctatcagtgatagagaacgtatctacagtttactccctatcagt gatagagaacgtatatccagtttactccctatcagtgatagagaacgtat aagctttaggcgtgtacggtgggcgcctataaaagcagagctcgtttagt gaaccgtcagatcgcctggaga |
| 15 | 5'- tttactccctatcagtgatagagaacgtatgaagagtttactccct atcagtgatagagaacgtatgcagactttactccctatcagtgatagaga |

FIG. 4 Continued

```
      acgtataaggagtttactccctatcagtgatagagaacgtatgaccagtt
      tactccctatcagtgatagagaacgtatctacagtttactccctatcagt
      gatagagaacgtatatccagtttactccctatcagtgatagagaacgtat
      aagctttaggcgtgtacggtgggcgcctataaaagcagagctcgtttagt
      gaaccgtcagatcgcctggaggtaatcaactaccaattccagctctcttt
      tgacaactggtcttataccaactttccgtaccacttcctaccctcgtaag
      acaattgcaa
16    5'- tttactccctatcagtgatagagaacgtatgaagagtttactccct
      atcagtgatagagaacgtatgcagactttactccctatcagtgatagaga
      acgtataaggagtttactccctatcagtgatagagaacgtatgaccagtt
      tactccctatcagtgatagagaacgtatctacagtttactccctatcagt
      gatagagaacgtatatccagtttactccctatcagtgatagagaacgtat
      aagctttaggcgtgtacggtgggcgcctataaaagcagagctcgtttagt
      gaaccgtcagatcgcctggagcaattccacaacactttgtcttatacca
      actttccgtaccacttcctaccctcgtaaa
17    5'- tttactccctatcagtgatagagaacgtatgaagagtttactccct
      atcagtgatagagaacgtatgcagactttactccctatcagtgatagaga
      acgtataaggagtttactccctatcagtgatagagaacgtatgaccagtt
      tactccctatcagtgatagagaacgtatctacagtttactccctatcagt
      gatagagaacgtatatccagtttactccctatcagtgatagagaacgtat
      aagctttaggcgtgtacggtgggcgcctataaaagcagagctcgtttagt
      gaaccgtcagatcgcctggagctaatcaactaccaattccagctctcttt
      tgacaactggtcttataccaactttccgtaccacttcctaccctcctaag
      acaattgcaaa
18    5'- gcctatgttcttttggaatctatccaagtcttatgtaaatgcttat
      gtaaaccataatataaaagagtgctgattttttgagtaaacttgcaacag
      tcctaacattcttctctcgtgtgtttgtgtctgttcgccatcccgtctcc
      gctcgtcacttatccttcacttttcagagggtcccccgcagatcccggt
      caccctcaggtcgg
19    5'- tttactccctatcagtgatagagaacgtatgaagagtttactccct
      atcagtgatagagaacgtatgcagactttactccctatcagtgatagaga
      acgtataaggagtttactccctatcagtgatagagaacgtatgaccagtt
      tactccctatcagtgatagagaacgtatctacagtttactccctatcagt
      gatagagaacgtatatccagtttactccctatcagtgatagagaacgtat
      aagcttgcctatgttcttttggaatctatccaagtcttatgtaaatgctt
      atgtaaaccataatataaaagagtgctgattttttgagtaaacttgcaac
      agtcctaacattcttctctcgtgtgtttgtgtctgttcgccatcccgtct
      ccgctcgtcacttatccttcacttttcagagggtcccccgcagatcccg
```

FIG. 4 Continued

```
       gtcaccctcaggtcgg
20     atgtaaat    (Oct-1₁)
       atgtaaac    (Oct-1₂)
21     tggaatctatccaa
22     atgtaaatgctt   (Fox A1₁)
       atgtaaaccat    (Fox A1₂)
23     5'- tttactccctatcagtgatagagaacgtatgaagagtttactccct
       atcagtgatagagaacgtatgcagactttactccctatcagtgatagaga
       acgtataaggagtttactccctatcagtgatagagaacgtatgaccagtt
       tactccctatcagtgatagagaacgtatctacagtttactccctatcagt
       gatagagaacgtatatccagtttactccctatcagtgatagagaacgtat
       aagcttccataatataaaagagtgctgattttttgagtaaacttgcaaca
       gtcctaacattcttctctcgtgtgtttgtgtctgttcgccatcccgtctc
       cgctcgtcacttatccttcacttttcagagggtcccccgcagatcccgg
       tcaccctcaggtcgg
24     5'- tttactccctatcagtgatagagaacgtatgaagagtttactccct
       atcagtgatagagaacgtatgcagactttactccctatcagtgatagaga
       acgtataaggagtttactccctatcagtgatagagaacgtatgaccagtt
       tactccctatcagtgatagagaacgtatctacagtttactccctatcagt
       gatagagaacgtatatccagtttactccctatcagtgatagagaacgtat
       aagcttccagggcgcctataaaagagtgctgattttttgagtaaacttgc
       aacagtcctaacattcttctctcgtgtgtttgtgtctgttcgccatcccg
       tctccgctcgtcacttatccttcacttttcagagggtcccccgcagatc
       ccggtcaccctcaggtcgg
25     5'- tttactccctatcagtgatagagaacgtatgaagagtttactccct
       atcagtgatagagaacgtatgcagactttactccctatcagtgatagaga
       acgtataaggagtttactccctatcagtgatagagaacgtatgaccagtt
       tactccctatcagtgatagagaacgtatctacagtttactccctatcagt
       gatagagaacgtatatccagtttactccctatcagtgatagagaacgtat
       aagctttgcttatgtaaccagggcgcctataaaagagtgctgattttttt
       gagtaaacttcaattccacaacacttttgtcttataccaactttccgtac
       cacttcctaccctcgtaaa
```

TETRACYCLINE INDUCIBLE TRANSCRIPTION CONTROL SEQUENCE

The present invention relates to inducible transcription control sequences for the regulation of gene expression. Specifically, it relates to a transcription control sequence comprising at least two tet operator sequence motifs allowing the binding of tetracycline-dependent transcriptional regulators, wherein each of the said tetracycline-dependent transcriptional regulators binds with respect to its neighbour to an opposite face of the DNA helix, and a minimal promoter comprising a TATA box which is linked at its 5' end to a general transcription factor binding site. Further, the present invention relates to a vector, a host cell, a plant or a non-human transgenic animal comprising the said transcription control sequence. Also contemplated is a method for regulating the expression of a nucleic acid sequence being operatively linked to the transcription control sequence of the present invention in a host cell, a plant or a non-human transgenic animal.

For the recombinant manufacture of polypeptides as well as for the control of gene expression in vivo, the exogenous control of the expression process (i.e. turning on or off the expression) is of particular importance. In this context, inducible systems for expression control are usually applied in order to achieve the said exogenous control. Specifically, expression of a certain nucleic acid can be governed by an exogenous stimulus. Such a stimulus may be a change in the physical culture conditions, such as a heat shock, or may be the presence or the absence (i.e. the withdrawal) of a certain compound.

A commercially and scientifically important inducible expression system is the so-called "tetracycline inducible system" or "Tet System". It has been developed by Bujard and co-workers more than a decade ago, see Gossen 1992, Proc Natl Acad Sci 89: 5547-5551, U.S. Pat. Nos. 5,888,981, 5,814,618, 6,004,941, 5,814,618, U.S. Ser. No. 10/456,395, WO96/01313 or WO00/75347.

In brief, the Tet System allows control of nucleic acid expression by using a promoter comprising tet operator sequences operatively linked to a nucleic acid to be expressed. Said promoter can initiate transcription of the nucleic acid sequence upon binding of a tetracycline-dependent transcriptional activator to the tet operator sequences or it may repress transcription of an otherwise constitutively active promoter upon binding of a tetracycline-dependent transcriptional silencer.

Traditionally, tetracycline-dependent regulators were known to bind to the tet operator sequence in the absence but not in the presence of tetracycline. Accordingly, expression could be initiated by the withdrawal of tetracycline or a tetracycline analog from, e.g., a culture medium of a cell line used for expression (U.S. Pat. Nos. 5,464,758, 6,914,124, 5,789,156, 6,271,348, WO96/01313, or WO00/75347).

Subsequently, tetracycline-dependent regulators were developed which allowed regulation in the opposite (reverse) manner. By using such regulators, expression can be initiated by the addition of tetracycline or an analog thereof to, e.g., a culture medium of a cell line used for expression (U.S. Pat. Nos. 5,654,168, 6,136,954, 5,789,156, 6,271,348, 6,087,166, 6,271,341, U.S. Ser. No. 10/456,395, WO96/01313, or WO00/75347).

Recent improvements of the Tet System focused on the tetracycline-dependent regulators. Specifically, improved regulators were developed which caused a lower basal activity but maintained a high induction potential. Thus, the induction factor was highly improved. Moreover, the maximal induction was achieved at lower concentrations of tetracycline or a tetracycline analog, see U.S. Ser. No. 10/456,395 or WO00/75347.

A tetracycline-dependent promoter comprising repositioned tet operator elements has been also reported, see Agha-Mohammadi 2004, J Gene Medicine, 6:817-828 or US2003/0221203. The disclosed promoter comprises a shortened CMV minimal promoter and between six and eight tet operator sequence motifs upstream of the minimal promoter.

However, a tetracycline-dependent transcription control sequence which allows for improved tight and reliable regulation, i.e. which has a low basal activity but still retains high induction potential, is not reported in the prior art and still highly desirable. Thus, the technical problem underlying the present invention may be seen as the provision of means and methods for improving inducible gene regulation whereby the drawbacks of high basal activity and improper or unreliable induction are avoided. The technical problem is solved by the embodiments characterized in the claims and herein below.

Generally, the present invention relates to a transcription control sequence comprising tet operator sequence motifs and a minimal promoter, whereby the said transcription control sequence allows for an at least 100-fold, at least 200-fold, at least 300-fold at least 400-fold, at least 500-fold or at least 1000-fold induction of the expression of a nucleic acid operatively linked thereto and whereby the transcription control sequence allows for a basal gene expression, i.e. gene expression in a non-induced status, which is significantly less than the basal activity of the commercially available Ptet-14 promoter (Clontech Laboratories Inc., US). The aforementioned induction and/or basal activity is, preferably, determined as described in the accompanying Examples, below.

The term "transcription control sequence" as used herein refers to a nucleic acid sequence which is capable of governing the expression of another nucleic acid sequence operatively linked thereto, such as a gene of interest. The transcription control sequence, preferably, is a DNA sequence, i.e. a DNA polynucleotide. The transcription control sequence according to the present invention shall comprise tet operator sequence motifs and minimal promoter sequences as specified in detail elsewhere herein. A transcription control sequence as referred to in accordance with the present invention, preferably, comprises sequence motifs which are recognized and bound by polypeptides, i.e. transcription factors. The said transcription factors shall upon binding recruit RNA polymerases, preferably, RNA polymerase I, II or III, more preferably, RNA polymerase II or III, and most preferably, RNA polymerase II. Thereby will be initiated the expression of a nucleic acid operatively linked to the transcription control sequence. It is to be understood that dependent on the type of nucleic acid to be expressed, expression as meant herein may comprise transcription of DNA sequences into RNA polynucleotides (as suitable for, e.g., anti-sense approaches, RNAi approaches or ribozyme approaches) or may comprise transcription of DNA sequences into RNA polynucleotides followed by translation of the said RNA polynucleotides into polypeptides (as suitable for, e.g., gene expression and recombinant polypeptide production approaches). In order to govern expression of a nucleic acid sequence, the transcription control sequence may be located immediately adjacent to the nucleic acid to be expressed, i.e. physically linked to the said nucleic acid at its 5' end. Alternatively, it may be located in physical proximity. In the latter case, however, the sequence must be located so as to allow functional interaction with the nucleic acid to be expressed.

The term "tet operator sequence motif", "tet operator", or "tetO" as used herein is intended to encompass all classes of tet operator sequences. Preferably, it relates to tetO(A), tetO (B), tetO(C), tetO(D), tetO(E), tetO(G), tetO(H), tetO(J) and tetO(Z). The nucleotide sequences of Tet repressors of members of the A, B, C, D, E, G, H, J and Z classes, and their corresponding tet operator sequences are well known in the art, see, for example, Waters 1983, *Nucl. Acids Res* 11:6089-6105, Hillen 1983, *Nucl. Acids Res*. 11:525-539, Postle 1984, *Nucl. Acids Res*. 12:4849-4863, Unger 1984, *Gene* 31: 103-108, Unger 1984, *Nucl Acids Res*. 12:7693-7703 and Tovar 1988, *Mol. Gen. Genet.* 215:76-80, which are incorporated herewith by reference with respect to the specifically disclosed tet operator sequences and in their entireties. Tet operator sequences are also disclosed in U.S. Pat. No. 5,464, 758. Preferred tet operator sequence motifs according to the present invention have a nucleic acid sequence as shown in SEQ ID NO: 1.

The term "minimal promoter" in the sense of the present invention relates to promoters which comprise nucleic acid sequence motifs which are specifically recognized by the DNA-binding general transcription factors involved in the formation of the transcription initiation complex. However, significant initiation of transcription and, thus, of expression of a nucleic acid sequence driven by a minimal promoter requires an additional signal, such as a signal conferred by an enhancer element. Accordingly, as referred to herein a minimal promoter by itself shall not allow for a transcription of a nucleic acid operatively linked thereto in a significant extent. However, upon combination of the said minimal promoter with suitable control elements, such as the tet operator sequence motifs referred to herein, the resulting transcription control sequence allows for transcription of a nucleic acid upon induction/activation of a tet operator-binding transcription factor such as the tetracycline-dependent transcriptional regulators referred to elsewhere herein.

In accordance with the present invention, the said minimal promoter, preferably, comprises a TATA Box sequence motif and at least one (further) general transcription factor binding site. Preferably, the TATA Box referred to herein consists of the nucleic acid sequence motif "TATAAAA" (SEQ ID NO: 4). The general transcription factor binding site is, preferably located adjacent to the TATA Box and, more preferably, located immediately adjacent to the 5' end of the TATA Box sequence. It is to be understood that the minimal promoter, preferably, already comprises a TATA Box as it is the case for the CMV minimal promoter. A general transcription factor binding site may not naturally occur in the minimal promoter. Accordingly, in such a case the said general transcription factor binding site is, preferably, artificially introduced in the minimal promoter, e.g., by site directed mutagenesis approaches. The term "further general transcription factor binding site" refers to nucleic acid sequence motifs except the TATA Box capable of binding to general transcription factors. General transcription factors are those transcription factors which are required to recruit RNA polymerases, and preferably, RNA polymerase II or III, to a promoter in order to initiate transcription. General transcription factors as well as the nucleic acid sequence motifs recognized and bound thereby are well known in the art. Preferably, general transcription factor binding sites in the sense of the present invention are binding sites for transcription factors which are involved in the formation of the pre-initiation complex with RNA polymerases and which are capable of interacting with the core promoter region (i.e. being DNA binding proteins).

More preferably, the further general transcription factor binding site referred to in accordance with the present invention is the TFIIB binding site (SEQ ID NO: 3).

Various well characterized minimal promoters are known in the art, e.g., minimal promoters of Mouse Mammary Tumor Virus (MMTV), Moloney Murine Leukemia Virus (MMLV), Human Immunodeficiency Virus (HIV) or Human Cytomegalovirus IE (hCMV) or non-viral minimal promoters. Such minimal promoters, if necessary, can be modified to comprise a TATA Box and a further general transcription factor binding site in accordance with the present invention by the skilled artisan without further ado.

Preferably, a minimal promoter referred to herein can be derived from the Cytomegalovirus (CMV) minimal promoter and, more preferably, from human CMV (hCMV) such as the hCMV immediate early promoter derived minimal promoter as described in, e.g., Gossen & Bujard 1992, loc. cit. More preferably, the said hCMV minimal promoter has a nucleic acid sequence as shown in SEQ ID NO: 2. Variants of such a hCMV minimal promoter can be used a well. Such a variant comprises a deletion, substitution and/or addition of at least one nucleotide with respect to the sequences shown in SEQ ID NO: 2. Accordingly, a variant, preferably, has a nucleic acid sequence which is at least 70%, at least 80%, at least 90%, at least 95%, at least 97, at least 98% or at least 99% identical to the sequences as shown in SEQ ID NO: 2. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution. 1987, 25, 351-360, and Higgins 1989, CABIOS, 5: 151-153) or the programs Gap and BestFit (Needleman 1970, J. Mol. Biol. 48; 443-453) and Smith 1981, Adv. Appl. Math. 2; 482-489), which are part of the GCG software packet (Genetics Computer Group, 575 Science Drive, Madison, Wis., USA 53711, version 1991) are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. Variants also encompass a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6×sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA: RNA hybrids are preferably, for example, 0.1×SSC and 30°

C. to 55° C., preferably between 45° C. and 55° C. The abovementioned hybridization temperatures are determined for example for a nucleic acid with approximately 100 by (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

A preferred minimal promoter derived from the hCMV minimal promoter having a TATA Box and a further general transcription factor binding site, namely a TFIIB binding site, is shown in SEQ ID NO: 5. A transcription control sequence carrying such a minimal promoter is $P_{tet}$-T2. It will be understood that variants of the said minimal promoter shown in SEQ ID NO: 5 having a nucleic acid sequence which is at least 70%, at least 80%, at least 90%, at least 95%, at least 97, at least 98% or at least 99% identical to the sequence as shown in SEQ ID NO: 5 or variants which hybridize thereto, preferably, under stringent hybridization conditions, are also contemplated by the present invention provided that the variants retain the properties of a minimal promoter as set forth above and comprise a TATA Box and a further general transcription factor binding site as referred to above.

Moreover, the minimal promoter shall be, preferably, modified by deletion or inactivation of a DSE element which is usually present in the CMV minimal promoter (Ghazal 1991, J. Virol. 65: 2299-2307). Specifically, the 5'-UTR of hCMV (i.e. nucleotide positions +1/75 of SEQ ID NO: 5) can be reduced in order to delete part of the DSE element located between nucleotide positions+33/50 of SEQ ID NO: 5 and sequences 3' to this element. A transcription control sequence carrying such a minimal promoter is $P_{tet}$-T3 (SEQ ID NO: 13). Furthermore, the 5'UTR of the CMV minimal promoter which is present 3' to the initiator sequence element between nucleotide positions +1/12 of SEQ ID NO: 5 is, also preferably, entirely deleted. A transcription control sequence carrying such a minimal promoter is $P_{tet}$-T4 (SEQ ID NO: 14). Accordingly, a preferred minimal promoter to be used for a transcription control sequence in accordance with the present invention has a nucleic acid sequence as shown in SEQ ID NO: 10. It will, of course, be understood that variants of the said minimal promoter shown in SEQ ID NO: 10 having a nucleic acid sequence which is at least 70%, at least 80%, at least 90%, at least 95%, at least 97, at least 98% or at least 99% identical to the sequence as shown in SEQ ID NO: 10 or variants which hybridize thereto, preferably, under stringent hybridization conditions, are also contemplated by the present invention provided that the variants retain the properties of a minimal promoter as set forth above and comprise a TATA Box and a further general transcription factor binding site as referred to above and the aforementioned further modifications.

Preferably, a minimal promoter referred to herein can be derived from the Mouse Mammary Tumor Virus (MMTV) minimal promoter as described in, e.g., Loew et al. 2006, loc. cit. More preferably, the said MMTV minimal promoter has a nucleic acid sequence as shown in SEQ ID NO: 18. Variants of such a MMTV minimal promoter can be used as well. Such a variant comprises a deletion, substitution and/or addition of at least one nucleotide with respect to the sequences shown in SEQ ID NO: 18. Accordingly, a variant, preferably, has a nucleic acid sequence which is at least 70%, at least 80%, at least 90%, at least 95%, at least 97, at least 98% or at least 99% identical to the sequences as shown in SEQ ID NO: 18 or a nucleic acid sequence which hybridizes thereto, preferably under stringent hybridization conditions. A transcription control sequence carrying such a MMTV minimal promoter is $P_{tet}$-T8 having a nucleic acid sequence as shown in SEQ ID NO: 19.

Moreover, the minimal promoter shall be, preferably, modified by deletion or inactivation of a upstream transcription factor binding sites, NF1, Fox A1 and Oct-1 (OTF-1) which were usually present in the MMTV minimal promoter (Cato 1988, J. Cell Biol., 106: 2119-2125; Xu 1994, Virus Res., 33: 167-178; Holmqvist 2005, Exp. Cell Res., 304:593-603; Belikov 2004, J. Biol. Chem., 279, 49857-49867). Specifically, the region 5'- to the TATA Box of MMTV (i.e. nucleotide positions −75/−62 (NF-1, SEQ ID NO: 21), −56/−45 (FoxA1$_1$, SEQ ID NO: 22), −44/−34 (FoxA1$_2$, SEQ ID NO: 22), −56/−49 (Oct1$_1$, SEQ ID NO: 20) and −44/−37 (Oct1$_2$, SEQ ID NO: 20) in SEQ ID NO: 18 can be deleted in order to eliminate this cis-elements from the minimal promoter. A transcription control sequence carrying such a minimal promoter is $P_{tet}$-T9 (SEQ ID NO: 23). It will, of course, be understood that variants of the said minimal promoter shown in SEQ ID NO: 23 having a nucleic acid sequence which is at least 70%, at least 80%, at least 90%, at least 95%, at least 97, at least 98% or at least 99% identical to the sequence as shown in SEQ ID NO: 23 or variants which hybridize thereto, preferably, under stringent hybridization conditions, are also contemplated by the present invention provided that the variants retain the properties of a minimal promoter as set forth above and comprise a TATA Box and a further general transcription factor binding site as referred to above and the aforementioned further modifications.

A further preferred minimal promoter derived from the MMTV minimal promoter having a TATA Box and a further general transcription factor binding site, namely a TFIIB binding site, is shown in SEQ ID NO: 3 and SEQ ID NO: 4. A transcription control sequence carrying such a minimal promoter is $P_{tet}$-T10 as shown in SEQ ID NO: 24. It will be understood that variants of the said transcription control sequence having a nucleic acid sequence which is at least 70%, at least 80%, at least 90%, at least 95%, at least 97%, at least 98% or at least 99% identical to the sequence as shown in SEQ ID NO: 24 or variants which hybridize thereto, preferably, under stringent hybridization conditions, are also contemplated by the present invention provided that the variants retain the properties of a minimal promoter as set forth above and comprise a TATA Box and a further general transcription factor binding site as referred to above.

The term "operatively linked" as used herein, in principle, means that two nucleic acids are either physically linked or are functionally linked so that at least one of the nucleic acids can act on the other nucleic acid. The transcription control sequence of the present invention and a nucleic acid sequence to be expressed, e.g., a gene of interest, are operatively linked if the expression of the nucleic acid sequence can be governed by the said transcription control sequence. Accordingly, the transcription control sequence and the nucleic acid sequence to be expressed may be physically linked to each other, e.g., by inserting the transcription control sequence at the 5'end of the nucleic acid sequence to be expressed. Alternatively, the transcription control sequence and the nucleic acid to be expressed may be merely in physical proximity so that the transcription control sequence is functionally linked to the nucleic acid sequence to be expressed. The transcription control sequence and the nucleic acid to be expressed are, preferably, separated by not more than 1,500 bp, 500 bp, 300 bp, 100 bp, 80 bp, 60 bp, 40 bp, 20 bp, 10 by or 5 bp.

It is to be understood that the expression of a nucleic acid operatively linked to the transcription control sequence of the present invention can be induced by contacting a host cell, non-human transgenic animal or plant comprising a tetracycline-dependent transcriptional regulator with tetracycline or an analog thereof as specified elsewhere in this description in detail.

Preferably, in order to determine the fold induction of a transcription control sequence as referred to in accordance with the present invention, a host cell can be made which expresses a tetracycline-dependent transcriptional regulator. The said cell line shall further comprise the transcription control sequence operatively linked to a nucleic acid sequence to be expressed, preferably, a reporter gene such as firefly luciferase. The transcription control sequence can be introduced into the cell line by techniques for stably transfecting cells known in the art. In order to determine the fold induction, the expression of the nucleic acid sequence shall be measured in a non-induced status and after induction. It is to be understood that induction can be achieved by contacting the host cells with tetracycline or an analog thereof in the case of a tetracycline-dependent regulator which binds in the presence of tetracycline or an analog thereof to the tet operator. In the case of a tetracycline dependent regulator which binds to the tet operator in the absence of tetracycline or an analog thereof, induction will be achieved by withdrawal of tetracycline or an analog thereof after the cells of the cell line have been previously contacted to the said tetracycline or analog thereof. Induced and basal (i.e. uninduced) transcriptional activities are measured by determining the amount of reporter gene activity (preferably, luciferase) 24 hours after addition or withdrawl of the effector molecule, i.e. tetracycline or an analog thereof. For such determinations, preferably, a reporter gene is used as the nucleic acid to be transcribed and the amount of transcripts is determined by measuring the amount of gene product or activity thereof of the reporter gene. Suitable reporter genes include, e.g., luciferase or chloramphenicol acetyl transferase. These principles of authentic and reverse regulation of gene expression using tetracycline-dependent transcriptional regulators are well known in the art and have been described in detail in U.S. Pat. Nos. 5,888,981, 5,814,618, 6,004,941, 5,814,618, U.S. Ser. No. 10/456,395, WO96/01313, or WO00/75347. The relative fold induction can be calculated as the ratio of the nuclei acid expression in the induced status to the nucleic acid expression in the non-induced status. More specifically, the fold induction of a transcription control sequence can be determined as described in the accompanying Examples in detail. Basal transcription of a transcription control sequence can be determined by comparing the amount of transcripts of a nucleic acid to be expressed in the uninduced state to the amount of transcripts of said nucleic acid to be expressed, transcribed in the uninduced state from a reference promoter, preferably, from $P_{tet}$-14 (Clontech Laboratories, Inc., US).

As used herein, "tetracycline analog" is intended to include compounds which are structurally related to tetracycline and which bind to the Tet repressor or the tetracycline dependent transcriptional regulators referred to herein below with a $K_a$ of at least about $10^{-6}$ M. Preferably, the tetracycline analog binds with an affinity of about $10^{-9}$ M or greater. Preferred tetracycline analogs are anhydrotetracycline (atc), doxycycline (dox), chlorotetracycline, oxytetracycline, or deoxytetracycline. Further analogs are disclosed by Hlavka and Boothe, "The Tetracyclines," in Handbook of Experimental Pharmacology 78, R. K. Blackwood et al. (eds.), Springer-Verlag, Berlin, N.Y., 1985; Mitscher, "The Chemistry of the Tetracycline Antibiotics", Medicinal Research 9, Dekker, N.Y., 1978; Noyee Development Corporation, "Tetracycline Manufacturing Processes" Chemical Process Reviews, Park Ridge, N.J., 2 volumes, 1969; Evans, "The Technology of the Tetracyclines," Biochemical Reference Series 1, Quadrangle Press, New York, 1968; and Dowling, "Tetracycline," Antibiotic Monographs, no. 3, Medical Encyclopedia, New York, 1955. In addition, tetracycline analogs encompass those which are disclosed in WO2007/133797 and WO2007/133798.

In light of the above, the present invention, more specifically, relates to a transcription control sequence comprising:
a) at least two tet operator sequence motifs allowing the binding of tetracycline-dependent transcriptional regulators, wherein each of the said tetracycline-dependent transcriptional regulators binds with respect to its neighbour to an opposite face of the DNA helix; and
b) a minimal promoter comprising a TATA box which is operatively linked at its 5' end to a general transcription factor binding site, preferably, a TFIIB binding site.

The term "at least two" as used herein, preferably, means two or more than two, i.e. at least three, at least four, at least five, at least six, at least seven or at least eight. A particular preferred number of tet operator sequence motifs to be included into the transcription control sequence of the present invention is seven.

It is envisaged that the said tetracycline-dependent regulators bind to adjacent tet operator sequence motifs in trans orientation, i.e. interact with opposing faces (or surfaces) of the DNA helix. Accordingly, the central nucleotides (central G in SEQ ID No. 1) of the at least two neighbouring tet operators are 36 nucleotides apart from each other equaling 3.5 helical turns. Thus, the spacer is, preferably, 17 contiguous nucleotides in length. It has been found in accordance with the present invention that such a spacer allows for an optimal configuration of the tetracycline dependent transcriptional activators upon binding to the tet operator sequence motifs. More preferably, the said spacer is free of cis-regulatory elements, palindromic sequences and/or splice sites. Said spacer can be obtained, preferably, by nucleic acid synthesis. Moreover, potential cis-regulatory elements can be identified by algorithms for nucleic acid sequence analysis well known in the art and described in detail, preferably, in Matys 2003, Nucleic Acids Res 31: 374-378. Preferably, the commercially available TRANSFAC Database, Release 7.0, from Biobase, Biological Databases GmbH, Germany shall be used. In general, cis-regulatory elements can be either deleted or inactivated, e.g., by introducing mutations into their consensus sequences, in order to generate a sequence being free of cis-regulatory elements according to this invention. Moreover, if more than one spacer is required, i.e. in cases where three or more tet operator sequence motifs shall be used, it is preferred that the spacer nucleic acid sequences separating the said tet operators have different nucleic acid sequences. Again, such spacers can be easily obtained by nucleic acid synthesis.

In a preferred embodiment of the transcription control sequence of the present invention, said minimal promoter is linked at its 3' end to a 5' UTR of the Turnip Yellow Mosaic Virus (TYMV). The said 5' UTR of the TYMV has a nucleic acid sequence as shown in SEQ ID NO: 11 or is a variant thereof comprising a deletion, substitution and/or addition of at least one nucleotide with respect to the sequence shown in SEQ ID NO 11. Such a variant, preferably, has a nucleic acid sequence being at least 70%, at least 80%, at least 90%, at least 95%, at least 97, at least 98% or at least 99% identical to the nucleic acid sequence shown in SEQ ID NO: 11 or hybridizes thereto, preferably, under stringent hybridization conditions. The sequence identity can be determined by the algorithms and techniques referred to above. A transcription control sequence carrying such a TYMV is $P_{tet}$-T5 (SEQ ID NO: 15). Preferably, the said 5' UTR of the TYMV is free of cis-regulatory elements as described elsewhere herein. More preferably, the TYMV 5'UTR is free of RFX-1 binding sites (SEQ ID NO: 6), AP4 binding sites (SEQ ID NO: 7), HP-1 binding sites (SEQ ID NO: 8), and/or HP-2 binding sites (SEQ ID NO: 9). The nucleic acid sequence motifs of the aforementioned transcription factor binding sites are also well known in the art (see Transfac Database). A transcription control sequence carrying a TYMV free of the said cis-regulatory elements is $P_{tet}$-T6 (SEQ ID NO: 16) and $P_{tet}$-T11 (SEQ ID NO: 25). A particularly preferred 5'UTR to be used for the transcription control sequence according to the present invention has, therefore, a nucleic acid sequence as shown in SEQ ID NO: 12. It will be understood that variants of the said 5'UTR having a nucleic acid sequence which is at least 70%, at least 80%, at least 90%, at least 95%, at least 97, at least 98% or at least 99% identical to the sequence as shown in SEQ ID NO: 12 or variants which hybridize thereto, preferably, under stringent hybridization conditions, are also contemplated by the present invention provided that the variants are also free of cis-regulatory elements and may serve as a 5'UTR.

Preferred transcription control sequences according to the present invention are those comprising a nucleic acid sequence as shown in any one of SEQ ID No. 13 to 17, 24 or 25 or variants thereof, wherein said variants may comprise a deletion, substitution or addition of at least one nucleotide with respect to the sequences shown in SEQ ID NO 13 to 17, 24 or 25. Accordingly, a variant, preferably, has a nucleic acid sequence which is at least 70%, at least 80%, at least 90%, at least 95%, at least 97, at least 98% or at least 99% identical to a sequence as shown in any one of SEQ ID No 13 to 17, 24 or 25 or a nucleic acid which is capable of hybridizing to the said specific sequences, preferably, under stringent conditions as referred to elsewhere herein. The sequence identity referred to before shall be, preferably, determined by the algorithms and techniques referred to elsewhere above. However, a variant transcription control sequence according to the present invention shall still comprise at least two tet operator sequence motifs and a minimal promoter which comprises a TATA Box and a further general transcription factor binding site, whereby the said transcription control sequence allows for an at least 100-fold induction of the expression of a nucleic acid operatively linked thereto and whereby the transcription control sequence allows for a basal gene expression, i.e. gene expression in a non-induced status, which is significantly less than the basal activity of the commercially available Ptet-14 promoter (Clontech Laboratories Inc., US). The structural elements of the aforementioned preferred transcription control sequences of SEQ ID NOs: 13 ($P_{tet}$-$T_3$), 14 ($P_{tet}$-T4), 15 ($P_{tet}$-$T_5$), 16 ($P_{tet}$-$T_6$) and 17 $P_{tet}$-$T_7$) are also shown in FIG. 1, below.

Most preferably, the transcription control sequence of the present invention has a nucleic acid sequence as shown in SEQ ID No.: 16 ($P_{tet}$-$T_6$) or a variant sequence thereof.

Moreover, in another preferred embodiment of the transcription control sequence of the present invention, said sequence is depleted of CpG islands, i.e. CG dinucleotides. Such an optimized transcription control sequence can, preferably, govern expression of a nucleic acid operatively linked thereto independently of genomic imprinting mechanisms and other potentially interfering epigenetic phenomena.

Advantageously, it has been found in accordance with the present invention that a transcription control sequence comprising at least two tet operator sequence motifs, a general transcription factor binding site and a TATA Box will have the superior properties referred to above, i.e. an increased level of induction and a reduced basal activity. A particular preferred transcription control sequence was found to comprise the following elements in a 5' to 3' order:

a) at least two tet operator sequence motifs allowing the binding of tetracycline-dependent transcriptional regulators, wherein each of the said tetracycline-dependent transcriptional regulators binds with respect to its neighbour to an opposite face of the DNA helix;

b) a minimal promoter comprising a general transcription factor binding site, preferably, TFIIB, which is operatively linked at its 3' end to a TATA box;

c) an un-translated (5'UTR) region being an initiator sequence element which is linked at its 5'end to the TATA box and which is, preferably, derived from the hCMV promoter; and d) an un-translated leader region (5'UTR) which is operatively linked at its 5'end to an initiator sequence and which, preferably, does not contain cis-regulatory elements interacting with unrelated transcriptional regulators.

The transcription control sequence of the present invention are found to be particularly useful for recombinant polypeptide production, anti-sense approaches, RNAi approaches or ribozyme approaches since a tight regulation is allowed. Moreover, due to the significantly reduced basal activity, the transcription control sequence of the present invention further qualifies for use in gene therapy.

The present invention, in principle, also contemplates a transcription control sequence comprising:

a) at least two tet operator sequence motifs allowing the binding of tetracycline-dependent transcriptional regulators, wherein each of the said tetracycline-dependent transcriptional regulators binds with respect to its neighbour to an opposite face of the DNA helix;

b) a minimal promoter; and.

c) a 5'UTR of the TYMV.

Specifically, it has been found that the superior properties of the transcription control sequence of the present invention are also conferred, in general, by the combination of a plant virus 5'UTR, i.e. the TYMV 5'UTR and the minimal promoter governed by the tet operator sequences. Preferred such transcriptional control sequences are $P_{tet}$-T8 (SEQ ID NO: 19) and $P_{tet}$-T9 (SEQ ID NO: 23) or variants thereof as specified above.

The present invention also relates to a vector comprising the transcription control sequence of the present invention.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such targeting constructs, preferably, comprise DNA of sufficient length for either homologous recombination or heterologous integration as described in detail below. The vector encompassing the transcription control sequence of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host cells.

In a preferred embodiment of the vector of the present invention, said vector is an expression vector. More preferably, in the vector of the invention, the transcription control sequence is operatively linked to a nucleic acid sequence to be expressed. Such operative linkage, preferably, allows expression of the said nucleic acid sequence in eukaryotic cells or isolated fractions thereof. In principle, regulatory elements ensuring expression in eukaryotic cells, preferably mammalian cells, are well known in the art. They, preferably, comprise regulatory sequences ensuring initiation of transcription as comprised by the transcription control sequence of the present invention as well as poly-A signals ensuring termination of transcription and stabilization of the transcript. Additional regulatory elements may be included into the vector such as transcriptional as well as translational enhancers. In this context, suitable expression vectors are known in the art such as vectors derived from retroviruses including lentiviruses, adenovirus, cytomegalovirus, adeno-associated viruses, measles virus, vaccinia virus, herpes viruses, or bovine papilloma virus, may be used for delivery of the vector of the invention into targeted cell population. Methods which are well known to those skilled in the art can be used to construct recombinant viral vectors; see, for example, the techniques described in Sambrook, Molecular Cloning—A Laboratory Manual, Cold Spring Harbor Laboratory (1989) N.Y. and Ausubel, Current Protocols in Molecular Biology, Green Publishing Associates and Wiley Interscience, N.Y. (1994).

In a further preferred embodiment of the vector of the present invention, said vector further comprises a polyadenylation signal. More preferably, the said polyadenylation signal is SV40 poly A, β-globin poly A, LTR poly A or growth hormone poly A.

Moreover, the present invention relates to a host cell comprising the transcription control sequence or the vector of the present invention.

As used herein, a "host cell" includes any cultivatable cell that can be modified by the introduction of heterologous DNA. Preferably, a host cell is one in which a transcriptional regulatory protein can be stably expressed, post-translationally modified, localized to the appropriate subcellular compartment, and made to engage the appropriate transcription machinery. The choice of an appropriate host cell will also be influenced by the choice of detection signal. For example, reporter constructs, as described above, can provide a selectable or screenable trait upon activation or inhibition of gene transcription in response to a transcriptional regulatory protein; in order to achieve optimal selection or screening, the host cell phenotype will be considered. A host cell of the present invention includes prokaryotic cells and eukaryotic cells. Prokaryotes include gram negative or gram positive organisms, for example, *E. coli* or *Bacilli*. It is to be understood that prokaryotic cells will be used, preferably, for the propagation of the transcription control sequence comprising polynucleotides or the vector of the present invention. Suitable prokaryotic host cells for transformation include, for example, *E. coli, Bacillus subtilis, Salmonella typhimurium*, and various other species within the genera *Pseudomonas, Streptomyces*, and *Staphylococcus*. Eukaryotic cells include, but are not limited to, yeast cells, plant cells, fungal cells, insect cells (e.g., baculovirus), mammalian cells, and the cells of parasitic organisms, e.g., trypanosomes. As used herein, yeast includes not only yeast in a strict taxonomic sense, i.e., unicellular organisms, but also yeast-like multicellular fungi or filamentous fungi. Exemplary species include *Kluyverei lactis, Schizosaccharomyces pombe*, and *Ustilaqo maydis*, with *Saccharomyces cerevisiae* being preferred. Other yeasts which can be used in practicing the present invention are *Neurospora crassa, Aspergillus niger, Aspergillus nidulans, Pichia pastoris, Candida tropicalis*, and *Hansenula polymorpha*. Mammalian host cell culture systems include established cell lines such as COS cells, L cells, 3T3 cells, Chinese hamster ovary (CHO) cells, embryonic stem cells, with BHK, HeK or HeLa cells being preferred. Eukaryotic cells are, preferably, used to for recombinant gene expression by applying the transcription control sequence or the expression vector of the present invention.

Further the present invention relates to a non-human transgenic animal comprising the transcription control sequence or the vector of the present invention.

A polynucleotide or vector comprising the transcription control sequence of the present invention, preferably, operatively linked to a nucleic acid to be expressed (i.e. a transgene) can be transferred into a fertilized oocyte of a non-human animal to create a non-human transgenic animal. The said non-human transgenic animal is capable of expressing the said nucleic acid in one or more cell types or tissues provided that the cells or tissue co-express a tetracycline dependent transcriptional regulator and are contacted by tetracycline or an analog thereof. A transgenic non-human animal as meant herein shall have cells that contain a transgene, wherein the transgene was introduced into the non-human animal or an ancestor of the said non-human animal at a prenatal, e.g., an embryonic, stage. A transgene is a DNA which is integrated into the genome of a cell from which a transgenic non-human animal develops and which remains in the genome of the mature non-human animal, thereby directing the expression of an encoded gene product in one or more cell types or tissues of the transgenic non-human animal. Preferred non-human transgenic animals are mammals, preferably rodents, mice and rats, farm animals including goats, sheep, pigs, cows, and horses, useful for large scale production of proteins (so called "gene farming") and insects. Insects can be used for so-called sterile insect control approaches. A transgenic non-human animal can be created, for example, by introducing a transgene into the male pronuclei of a fertilized oocyte, e.g., by microinjection, and allowing the oocyte to develop in a pseudopregnant female foster animal. Methods for generating transgenic animals, particularly animals such as mice, have become conventional in the art and are described, for example, in U.S. Pat. Nos. 4,736,866 and 4,870,009 and Hogan 1986, A Laboratory Manual, Cold Spring Harbor, N.Y., Cold Spring Harbor Laboratory. A transgenic founder animal can be used to breed additional animals carrying the transgene. Transgenic animals carrying a transgene according to the present invention can further be bred to other transgenic animals carrying other transgenes, e.g., to a transgenic animal which expresses a polynucleotide encoding a tetracycline-dependent transcripitional regulator (discussed in more detail herein below). The invention also provides a homologous recombinant non-human animal comprising the vector or transcription control sequence of the present invention, preferably in form of a transgene, as referred to above. In such a non-human homologous recombinant animal, said nucleic acids have been introduced into a specific site of the genome, i.e., the nucleic acid molecule has homologously recombined with an endogenous gene or other part of the genome. In said case, the animal, preferably, is a mouse. To create such a homologous recombinant animal, preferably, a vector is prepared which contains DNA encoding the nucleic acid to be introduced flanked at its 5' and 3' ends by additional nucleic acids of a gene or part of the genome at which homologous recombination shall occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, 1987, Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li 1992, Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E.J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA. These "germline transmission" animals can further be mated to animals carrying a gene encoding a tetracycline dependent transcriptional regulator. In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis 1993, Nucl. Acids Res. 21:2025-2029; and Fukushige 1992, Proc. Natl. Acad. Sci. USA 89:7905-7909) and the FLP recombinase-FRT target system (e.g., as described in Dang 1992, Dev. Genet. 13:367-375; and Fiering 1993, Proc. Natl. Acad. Sci. USA 90:8469-8473).

The present invention also relates to a transgenic plant comprising the transcription control sequence or the vector of the present invention.

The term "plant" as used herein encompasses plants and algae. Preferably, the term relates to multicellular land plants. More preferably, the multicellular land plants are higher plants such as crop plants including maize, canola, soybean, rice, tagetes, brassica, tricium, or glycine. In principle, transgenic plants can be obtained as described in Becker 1992, Plant Mol. Biol. 20:1195-1197, Bevan 1984, Nucleic Acids Res. 12:8711-8721, and "Vectors for Gene Transfer in Higher Plants" in: Transgenic Plants, Vol. 1, Engineering and Utilization, eds.: Kung and R. Wu, Academic Press, 1993, p. 15-38. Preferably, transformation of plant cells and, thus, generation of transgenic plants, will be achieved by *Agrobacterium*-mediated transformation or by applying physical forces (e.g. "gene gun").

In addition, the present invention relates to a method for regulating the expression of a nucleic acid sequence being operatively linked to the transcription control sequence of the present invention in a host cell, a plant or a non-human transgenic animal comprising:
a) expressing in the said host cell, plant or non-human transgenic animal a polynucleotide encoding a tetracycline-dependent transcriptional regulator; and b) modulating the concentration of a tetracycline or analog thereof in the said host cell, plant or non-human transgenic animal.

The polynucleotide encoding a tetracycline-dependent transcriptional regulator can be expressed in the host cell, plant or animal by any means allowing expression of the tetracycline-dependent transcriptional regulator from the polynucleotide. It is to be understood that as a result of the expression, tetracycline-dependent transcriptional regulator polypeptides shall be present in the host cell, the plant or the non-human transgenic animal in an amount sufficient to govern expression of the nucleic acid sequence linked to the transcription control sequence. A polynucleotide encoding the tetracycline dependent transcriptional regulator may to this end be transiently or stably introduced into the said host cell, plant or animal by techniques well known in the art and described, e.g., in U.S. Pat. Nos. 5,888,981, 5,814,618, 6,004, 941, 5,814,618, 5,854,310, 5,866,755, 5,912,411, 5,866,755, 6,252,136, 6,242,667, U.S. Ser. No. 10/456,395, WO96/01313, or WO00/75347. Moreover, it may be introduced in the case of plants or animals by cross-breeding and in the case of host cells by cell fusions. Alternatively, the polynucleotide encoding the tetracycline-dependent transcriptional regulator may be introduced, e.g., by viral vectors.

A tetracycline-dependent transcriptional regulator as referred to in accordance with the method of the present invention is a polypeptide and, preferably, a fusion polypeptide comprising a domain which is capable of specifically recognizing the tet operator sequence motif. Moreover, the tetracycline-dependent transcriptional regulator shall further comprise a domain which governs expression of a nucleic acid sequence, i.e. a transactivating or silencing domain. The binding of tetracycline-dependent transcriptional regulator to the tet operator is, furthermore, dependent on the presence or absence or the amount of tetracycline or an analog thereof. The Tet repressor, first characterized in bacteria, contains a tet operator binding domain. Moreover, its binding to the tet operator is dependent on tetracycline or an analog thereof. Specifically, in the presence of tetracycline or an analog thereof, no binding will occur (so-called "Tet repressor") while in the absence of tetracycline or an analog thereof, the affinity of the Tet repressor for the tetO increases and binding will occur. Various variants of the Tet repressor have been generated. In particular, one type of variants have been described which bind to the tet operator in the presence but not the absence of tetracycline (so-called "reverse Tet repressor"). For the control of expression in eukaryotes, the aforementioned Tet repressor variants shall be fused to transactivating domains, e.g., of the VP-16 transactivator (see, e.g., U.S. Pat. No. 6,087,166 or U.S. Pat. No. 6,271,341), or to silencing domains, e.g., of krüppel-related transcription factors. For details relating to Tet repressors or variants thereof, see U.S. Pat. Nos. 5,464,758, 6,914,124, 5,789,156, 6,271, 348, 5,654,168, 6,136,954, 5,789,156, 6,271,348, 6,087,166, 6,271,341, U.S. Ser. No. 10/456,395, WO96/01313 or WO00/75347).

In a preferred embodiment of the method of the present invention, said tetracycline-dependent transcriptional regulator binds to the tet operator in the absence of tetracycline or analog thereof (so-called "authentic tetracycline-dependent transcriptional activators" or "tTA"). Preferred tetracycline-dependent transcriptional regulators having said properties are disclosed in U.S. Pat. Nos. 5,464,758, 6,914,124, 5,789, 156, 6,271,348, WO96/01313, or WO00/75347 which are herewith incorporated by reference.

In another preferred embodiment of the method of the present invention, said tetracycline-dependent transcriptional regulator binds to the tet operator in the presence of tetracycline or analog thereof (so-called "reverse tetracycline-dependent transcriptional activators" or "rtTA"). Preferred tetracycline-dependent transcriptional regulators having said properties are disclosed in U.S. Pat. Nos. 5,654,168, 6,136, 954, 5,789,156, 6,271,348, 6,087,166, 6,271,341, U.S. Ser. No. 10/456,395, WO96/01313, or WO00/75347 which are herewith incorporated by reference.

More preferably, the aforementioned tetracycline-dependent transcriptional regulator activates (see U.S. Pat. Nos. 5,464,758, 6,914,124, 5,654,168, 6,136,954, 6,087,166, 6,271,341, U.S. Ser. No. 10/456,395, WO96/01313, or WO00/75347, incorporated herewith by reference) or inhibits (see U.S. Pat. Nos. 5,789,156, 6,271,348, 5,789,156, 6,271, 348, U.S. Ser. No. 10/456,395, WO96/01313, or WO00/75347, incorporated herewith by reference) expression of the nucleic acid sequence.

The term "modulating the concentration of a tetracycline or analog thereof" as used herein means altering the concentration of the tetracycline or analog thereof. Specifically, if a tetracycline-dependent transcriptional regulator which binds to the tet operator in the presence of tetracycline or analog thereof is to be used in the method of the present invention, the expression of the nucleic acid to be expressed can be achieved by adding de novo an amount of tetracycline or by increasing the amount of tetracycline present in the host cell, plant or non-human transgenic animal. Vice versa, if a tetracycline-dependent transcriptional regulator which binds to the tet operator in the absence of tetracycline or analog thereof is to be used, the tetracycline amount present in the host cell, plant or non-human transgenic animal shall be lowered or tetracycline may be withdrawn entirely. Tetracycline or an analog thereof may be delivered to the host cell, preferably, via the culture medium which comprises the host cells. In the case of plants, tetracycline or an analog thereof may be delivered to the individual cells of the plant or non-human transgenic animal by water or nutrient supply or via infusions. These techniques are well known to the person skilled in the art and can be adopted for individual conditions without further ado.

As set forth above, the transcription control sequence may be used for human or non-human gene therapy of various diseases or disorders. Thus, the present invention also includes a pharmaceutical composition comprising the transcription control sequence, the vector or the host cell of the present invention and, preferably, a pharmaceutically acceptable carrier. More specifically, the transcription control sequence of the present invention shall be operatively linked to a nucleic acid sequence which, upon expression, will be therapeutically effective. Accordingly, the pharmaceutical compositions referred to herein above will further comprise a nucleic acid which is in operative linkage to the transcription control sequence and which encodes a therapeutically effective polypeptide or which can be expressed as a therapeutically effective polynucleotide, such as antisense RNA or RNAi.

The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. The polynucleotides, i.e. the transcription control sequence or vector of the present invention, may be administered in a gene therapy approach by using viral vectors, viruses or liposomes. Host cells may be implanted by operative techniques or infusion.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

Preferably, the pharmaceutical composition provides a therapeutically effective dose of the ingredients. A therapeutically effective dose refers to an amount of ingredients which prevents, ameliorates or treats the symptoms accompanying a disease or condition to be treated. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. It will be understood that the therapeutically effective agent in the present case will be the nucleic acid to be expressed. However, since the expression of said nucleic acid is tightly controlled by the transcription control sequence of the present invention, the said transcription control sequence needs to be provided in a therapeutically acceptable and effective amount as well.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

The transcription control sequence of the present invention may be provided together with other components required for expression of nucleic acids in a tetracycline inducible system as a kit adopted for carrying out the method of the present invention. Other components of a kit are, preferably, tetracycline or an analog thereof, a tetracycline-dependent transcriptional regulator or polynucleotide encoding it, e.g., in the form of an expression vector, and/or a host cell to be used for expression.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the said methods. The instructions can be provided by a users manual in paper- or electronic form. For example, the manual may comprise instructions for interpreting the results obtained when carrying out the aforementioned methods using the kit of the present invention.

Explanations on the sequence identification numbers (SEQ ID NOs) referred to herein above is given in the following:

| SEQ ID NO: | explanation |
|---|---|
| 1 | tet operator |
| 2 | hCMV minimal promoter |
| 3 | TFIIB binding site |
| 4 | TFIID binding site, TATA Box |
| 5 | minimal promoter from Ptet-T2 |
| 6 | RFX-1 binding site |
| 7 | AP4 binding site |
| 8 | HP-1 binding site |
| 9 | HP-2 binding site |
| 10 | Modified minimal promoter from Ptet-T4 |
| 11 | TYMV 5'UTR |
| 12 | Modified TYMV 5'UTR from Ptet-T6 |
| 13 | Ptet-T3 |
| 14 | Ptet-T4 |
| 15 | Ptet-T5 |
| 16 | Ptet-T6 |
| 17 | Ptet-T7 |
| 18 | MMTV minimal promoter |
| 19 | Ptet-T8 |
| 20 | Oct-1₁ Oct1₂ (OTF-1) binding sites |
| 21 | NF 1 binding site |
| 22 | FOX A1 binding site |
| 23 | Ptet-T9 |
| 24 | Ptet-T10 |
| 25 | Ptet-T11 |

All references cited in this specification are herewith incorporated by reference with respect to their entire disclosure content and the disclosure content specifically mentioned in this specification.

The figures show:

FIG. 1: Sequence comparison of the transcription control sequences $P_{tet}$-T1, $P_{tet}$-T2, $P_{tet}$-T3, $P_{tet}$-T4, $P_{tet}$-T5, $P_{tet}$-T6 and $P_{tet}$-T7. Sequence alignment of minimal promoters used in the regulatory units Ptet-T1 to -T7. Variations of the promoter sequence after modification of the hCMV minimal promoter T1 (=$P_{tet-1}$). Mutations of the original sequence are shown in bold, deletions were shown by dashes. Similar, sequence modifications in the plant viral leader (TYMV) were shown in blue, while deletions were indicated by dashes. Common to all constructs is the TATA-box and hCMV initiator sequence (+1/+12, yellow)) covering the transcriptional start site. Beginning with T2, a TFIIB consensus binding site was introduced. Also in common were the cloning sites (underlined) at the Hin dIII (5') and Sal I (3'). The T1 to T4 promoters contain the hCMV 5'-UTR and variations of it, while T5 to T7 promoters contain the TYMV 5'-UTR and variations of it. The TYMV-leader used, comprises sequences from +2-90 of the viral sequence. The SEQ ID NOs for the aligned sequences is indicated in brackets after the sequences.

FIG. 2: Luciferase induction and basal activity in the induced and non-induced state of Ptet-T1->Ptet-T6.

Figure 3:
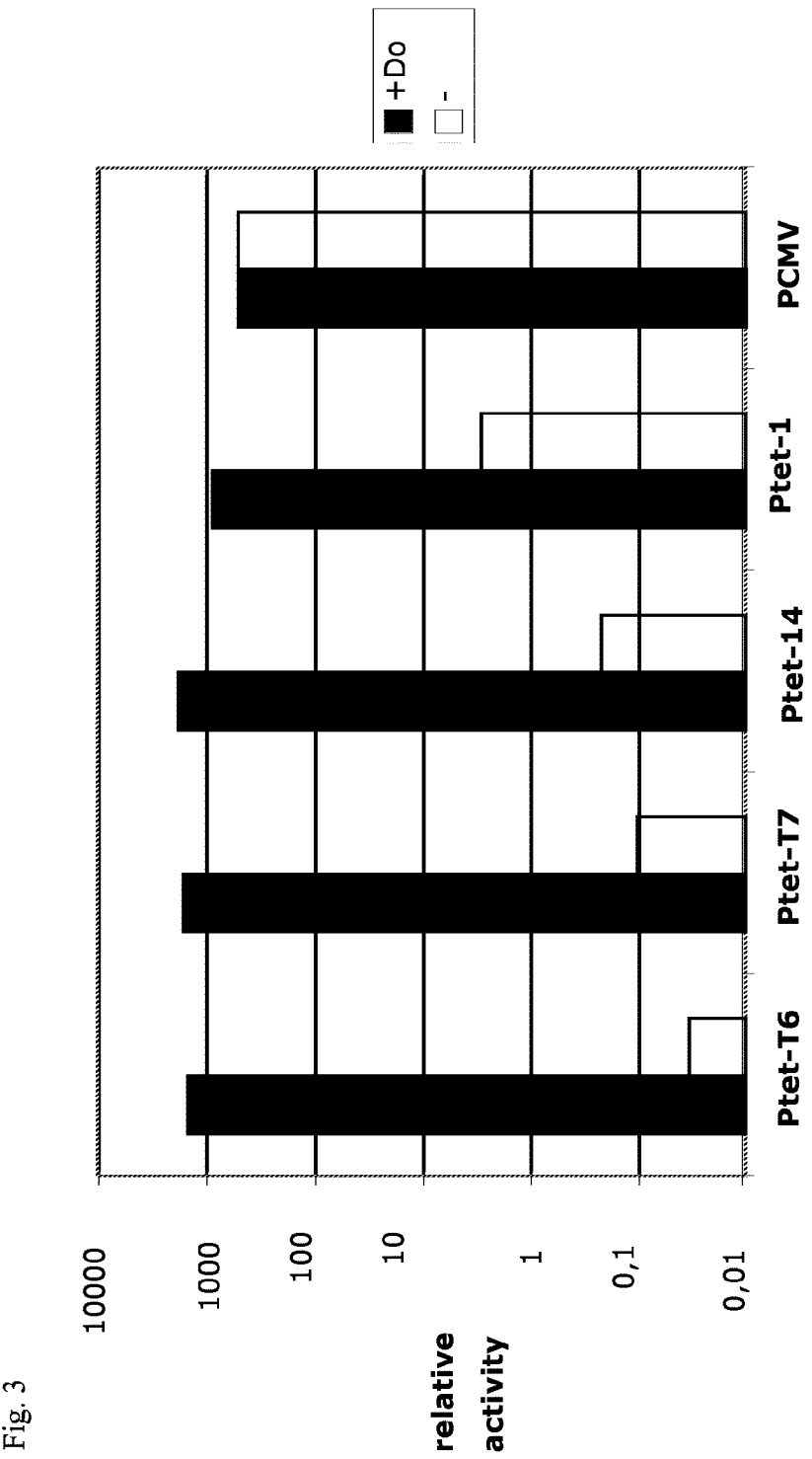

FIG. 3: Luciferase induction and basal activity in the induced and non-induced state of Ptet-T6, Ptet-T7, Ptet-14, (commercially available from Clontech Laboratories, Inc. US) Ptet-1 (Gossen 1992, loc. cit.) and a constitutively expressed reporter construct (PhCMV) were analysed under identical conditions.

FIG. 4: Synthetic sequences of $P_{tet}$-T6. A shows a synthetic (CpG island free) sequence of $P_{tet}$-T6 ($P_{tet}$-T6$^{syn}$), nucleotide changes compared to Ptet-T6 are lower case, underlined, and introduced to remove CpG dinucleotides, the two sequences correspond too fragment 1 (SEQ ID NO:65) and fragment 2 (SEQ ID NO:66) of Ptet-T6$^{syn}$; B shows a bidirectional $P_{tet}$-T6$^{syn}$. TATA Boxes are also underlined, the three sequences correspond to fragment 1 (SEQ ID NO:67), fragment 2(SEQ ID NO:68) and fragment 3 (SEQ ID NO:69) of bidirectional Ptet-T6.

The following Examples shall merely illustrate the invention. They shall not be construed, whatsoever, to limit the scope of the invention.

EXAMPLE 1

Generation of Tetracycline Dependent Transcription Control Sequence with Lower Basal Activity and Better Induction Potential I) Synthesis of the Tet-Operator Heptamer and Linkage to Minimal Promoters Oligonucleotides were synthesized and pairs (TOH-1 to TOH-6, see below Table 1) were annealed. The ds-oligos TOH-1-TOH-6 were PAGE-purified and ligated. The initial synthesis of the complete operator heptamer including one of the minimal promoters (T3) is shown below.

The synthesis is started with TOH-2/TOH-3 and TOH-4/TOH-5 ligation. The ligated pairs were PAGE-purified and the resulting DNA fragments TOH-2.3 and TOH-4.5 were ligated. The resulting DNA fragment (TOH-2.3.4.5) again PAGE purified and ligated to TOH-1 and after purification (TOH-1.2.3.4.5) to TOH-6. This final ligation resulted in the TO7 fragment (subsequently termed $P_{tet}$-T3), that provides 5' a Xho 1 and 3' a Nco I restriction site for direct insertion into the SK-eGFP plasmid (see below).

TABLE 1

List of oligonucleotide pairs. The SEQ ID NOs indicated below the box are allocated to the upper and lower sequence, respectively.

```
pair: TOH-1
5'-TCGAGtttactccctatcaGtgatagagaacgtatGaaGAGtttactccctatcaGtgataga
3'-     CaaatgagggatagtCactatctcttgcataCttCTCaaatgagggatagtcac
```

SEQ ID NO: 26

SEQ ID NO: 27

```
pair: TOH-2
5'-     gaacgtatGcaGActttactccctatcaGtgatagagaacgtataagGAGtttactccc
3'-tatctcttgcataCgtCTGaaatgagggatagtCactatctcttgcatattcCTcaaat
```

SEQ ID NO: 28

SEQ ID NO: 29

TABLE 1-continued

```
pair: TOH-3
5'-    tatcaGtgatagagaacgtatGaCcAGtttactccctatcaGtgatagagaacgtat
3'-gagggatagtCactatctcttgcataCtGgTCaaatgagggatagtCactatctcttgcatagAtG
```
SEQ ID NO: 30
SEQ ID NO: 31

```
pair: TOH-4
5'-cTaCAGtttactccctatcaGtgatagagaacgtataTCcAGtttactccctatcaGtgata
3'-     TCaaatgagggatagtCactatctcttgcatatAGgTCaaatgagggatagtCactatctct
```
SEQ ID NO: 32
SEQ ID NO: 33

```
pair: TOH-5
5'-gagaacgtatAAGCTTTAGGCGTGTACGGTgggcgcctataaaaGCAGAGCTCGTTTAGTGAACC
3'-tgcataTTCGAAATCCGCACATGCCAcccgcggatattttCGTCTCGAGCAAATCA
```
SEQ ID NO: 34
SEQ ID NO: 35

```
pair: TOH-6
5'-GtCAGATCGCCTGGAGACGCCATCCACGCTGTTTTGACCTCCATAGAAGAgtcgacAC
3'-CTTGGCaGTCTAGCGGACCTCTGCGGTAGGTGCGACAAAACTGGAGGTATCTTCTcagctgTGGcat-
```
SEQ ID NO: 36
SEQ ID NO: 37

The synthetic TO7 PCR-fragment was digested with Xho I/Nco I restriction enzymes. It is inserted into the similarly digested SK-eGFP plasmid (pBluescript SKII+ based). This plasmid already contained the open reading frame (orf) of the PCR-amplified enhanced green fluorescent protein (eGFP) and provides the Xho I/Nco I restriction sites for the direct introduction of the regulatory unit 5'- to the orf. The resulting plasmid was termed SK-TO7.g. This plasmid served as basis for insertion of all minimal promoter variants either as Hin d III/Sal I (T1 and T2) fragments, as annealed ds-Oligos (T4) or via Ex-site mutagenesis (T3, T5, T6 and T7), 3' to the new tet-operator (Hin d III) and 5' to the eGFP reporter gene (Sal I).

The new regulatory units that were generated by insertion of the minimal promoter variants into SK-TO7.g were termed $P_{tet}$-T1 to $P_{tet}$-T7, to indicate the fact that they were fused to the newly designed tet-operator heptamer.

The $P_{tet}$-T1 promoter contained the CMV minimal promoter (−53/+75) as described earlier (Gossen and Bujard, 1992 loc. cit.) and was released as Hin d III/Sal I from a subclone and introduced into similar digest SK-TO7.g plasmid.

The $P_{tet}$-T2 promoter was created by site directed mutagenesis of SK-Ptet-T1.g. A mutational oligonucleotide was designed, that replaced "ag" dinucleotide for "c" upstream of the TATA-box, creating the TFIIB binding site and to exchange the "t" at position −25 to "a" in order to create a TATA-box consensus sequence.

The $P_{tet}$-T3 promoter was generated in PCR via Ex-site mutagenesis with overlapping oligonucleotides (listed below, table 2) and SK-TO7.g plasmid as template. No additional cloning step was necessary after PCR reaction and religation of the plasmid.

The $P_{tet}$-T4 promoter was created as a doublestrand oligonucleotide (listed below, table 2) providing Hin d III and Sal I overhangs, which was inserted into the Hin d III/Sal I digested SK-TO7.g plasmid.

The $P_{tet}$-T5, $P_{tet}$-T6 and $P_{tet}$-T7 promoters were generated in PCR via Ex-site mutagenesis with overlapping oligonucleotides (listed below, table 2) and SK-TO7.g plasmid as template. No additional cloning step was necessary after the PCR reaction and religation of the plasmids.

TABLE 2

Oligonucleotides used for the introduction of minimal promoter variants into the basic SK-TO7.g plasmid.

| Promoter | Oligonucleotide | Sequence |
| --- | --- | --- |
| T3 | TO7.s (SEQ ID NO: 38) | 5'-CCTCCATAGAAGAgtcgacaccatggtgagc |
|  | TO7.as (SEQ ID NO: 39) | 5'-AAACAGCGTGGATGGCGTCTCCAGGCGATCTGaCG |
| T4 | TO7.1s (SEQ ID NO: 40) | 5'-agcttTAGGCGTGTACGGTGGGCGCCTATAAAAGCAGAGC TCGTTTAGTGAACCGtCAGATCGCCTGGAGAgtcgacac |
|  | TO7.1as (SEQ ID NO: 41) | 5'-catggtgtcgacTCTCCAGGCGATCTGaCGGTTCACTAAA CGAGCTCTGCTTTTATAGGCGCCCACCGTACACGCCTAa |
| T5 | TO7.2s (SEQ ID NO: 42) | 5'-ATACCAACTTTCCGTACCACTTCCTACCCTCGTAAGACAA TTGCAAgtcgacaccatggtgagc |
|  | TO7.2as (SEQ ID NO: 43) | 5'-AAGACCAGTTGTCAAAAGAGAGCTGGAATTGGTAGTTGAT TACctccAggcgatctgacg |

TABLE 2-continued

Oligonucleotides used for the introduction of minimal promoter variants into the basic SK-TO7.g plasmid.

| Promoter | Oligonucleotide | Sequence |
|---|---|---|
| T6 | TO7.3s (SEQ ID NO: 44) | 5'-CTTTCCGTACCACTTCCTACCCTCGTAAAgtcgacaccat ggtgagc |
|  | TO7.3as (SEQ ID NO: 45) | 5'-TTGGTATAAGACAAAAGTGTTGTGGAATTG<u>ctccaggcga tctgacg</u> |
| T7 | TO7.4s (SEQ ID NO: 46) | 5'-CAACTTTCCGTACCACTTCCTACCCTCCTAAGACAATTGC AAAgtcgacaccatggtgagc |
|  | TO7.4as (SEQ ID NO: 47) | 5'-GTATAAGACCAGTTGTCAAAAGAGAGCTGGAATTGGTAGT TGATTAG<u>ctccaggcgatctgacg</u> |
| T8 | MMTV-5' (–89) (SEQ ID NO: 48) | 5'-accgaagcttGCCTATGTTCTTTTGGAATC |
|  | MMTV-3' (+122) (SEQ ID NO: 49) | 5'-CCCGGTCACCCTCAGGTCGGgtcgacaccatggccagatat cccc |
| T9 | MMTV-5' (–37) (SEQ ID NO: 50) | 5'-accgaagcttCCATAATATAAAAGAGTGCTG |
|  | MMTV-3' (+122) (SEQ ID NO: 51) identical with T8 | 5'-CCCGGTCACCCTCAGGTCGGgtcgacaccatggccagatat cccc |
| T10 | TO7.7-s (SEQ ID NO: 52) | 5'-atcaagcttCCAGGGCGCCTATAAAAGAGTGCTGATTTTTTG |
|  | TO7.7-as (SEQ ID NO: 53) | 5'-atccatggtgtcgacCCGACCTGAGGGTGAC |
| T11 | TO7.8-s1 (SEQ ID NO: 54) | 5'-atcaagcttTGCTTATGTAAACCAGGGCGCCTATAAAAGAGT |
|  | TO7.8-as1 (SEQ ID NO: 55) | 5'-GTGGAATTGAAGTTTACTCAAAAAATCAGC<u>ACTCTTTTATA GGCGCCCT</u> |
|  | TO7.8-s2 (SEQ ID NO: 56) | 5'-<u>TGAGTAAACTTCAATTCCAC</u>AACACTTTTGTCTTATACCA ACTTTCCGTACC |
|  | TO7.8-as2 (SEQ ID NO: 57) | 5'-atccatggtgtcgacTTTACGAGGGTAGGAAGT<u>GGTACGGA AAGTTGGTATA</u> |

The overlap to the CMV-initiator sequence (+1/+12 in all promoters of T1-T7), the eGFP open reading frame or between complementary oligonucleotides for template-free synthesis of a minimal promoter (T11) is underlined. The restriction sites (5'-Hin d III and 3'-Sal I) were shown in bold. The introduced promoter sequences were in upper case letters. The T4 oligonucleotides include the whole promoter. T8 and T9 oligonucleotides were used for PCR-adaption of the minimal promoter sequences.

The synthesis of the $P_{tet}$-T8 minimal promoter was performed with MMTV-5' (–89) and MMTV-3' oligos (s. table 2) and pΔMtetO-luc (Hoffmann 1997, Nucleic acids Res., 25, 1078-1079) as template. The minimal promoter (–88/+122) was subcloned into pBluescript SK II+plasmid and sequenced. Functionality of this minimal promoter in the context of tet-regulated promoters was already published (Loew 2006, loc cit.). The minimal promoter was fused to the new tet-operators in SK-TO7.g plasmid via insertion as Hin dIII/Sal I fragment into similar digested plasmid. The resulting plasmid is termed SK– R, TO7.5. Release of $P_{tet}$-T8 promoter is possible as (5') Xho I/Sal I or Nco I (3') fragment.

The $P_{tet}$-T9 promoter was generated in PCR via amplifikation of the whole promoter with MMTV-5'(–37) and MMTV-3' oligo (s. table 2) and SK-MMTV (–88/+122) as template. The minimal promoter (–37/+122) was subcloned into pBluescript SK II+plasmid and sequenced. Fusion of the $P_{tet}$-T9 minimal promoter to the new tet-operators in SK-TO7.g plasmid was done via insertion as Hin dIII/Sal I fragment into similar digested plasmid. The resulting plasmid is termed SK-TO7.6. Release of Ptet-T9 promoter is possible as (5') Xho I/Sal I or Nco I (3') fragment.

The synthesis of the $P_{tet}$-T10 minimal promoter was done via PCR with TO7.7s and TO7.as (s. table 2) oligonucleotides and SK-MMTV(–37/+122) plasmid as template. The TFIIB and TATA consensus sequences were introduced by the 5'-oligo, together with the Hin dIII restricion site. Similar, the Sal I and Nco I restriction sites were introduced by the 3'-oligo. The resulting amplified promoter fragment (–41/+122) was termed "T10". The minimal promoter was digested with Hin dIII and Sal I and inserted directely into SK– TO7.g and sequenced. Thus, fusion of the $P_{tet}$-T10 minimal promoter to the new tet-operators in SK-TO7.g plasmid was done via insertion as Hin dIII/Sal I fragment into similar digested plasmid. The resulting plasmid is termed SK-TO7.7. Release of $P_{tet}$-T10 promoter is possible as (5') Xho I/Sal I or Nco I (3') fragment.

The synthesis of $P_{tet}$-T11 minimal promoter will be done with overlapping oligos in PCR without template. Within the final $P_{tet}$-T11 minimal promoter, sequences of the $P_{tet}$-T6 minimal promoter that originated from CMV promoter were replaced by MMTV sequences. However, it should be noted, that by this measure, the Oct-$1_2$ and the overlapping Fox A$1_e$ recognition sites were reintroduced to the minimal promoter. This modification was performed by oligonucleotide-based synthesis. The TO7.8-s1 and TO7.8-as1 oligos were annealed and 3'-ends blunted by DNA synthesis via T4-polymerase, separated by polyacrylamid gel electrophoresis followed by purification of the double stranded oligo. Similar, the TO7.8-s2 and TO7.8-as2 oligos were annealed, blunt-ended and purified. Finally, the two ds-oligonucleotides were mixed at an aquimolar ratio (1pmol each) and PCR-amplification was performed. The resulting amplified promoter fragment was termed "T11". The minimal promoter was digested with Hin dIII and Sal I and inserted directely into SK-TO7.g and sequenced. Thus, fusion of the $P_{tet}$-T11 minimal promoter to the new tet-operators in SK-TO7.g plasmid was done via insertion as Hin dIII/Sal I fragment into similar digested plasmid. The resulting plasmid is termed SK-TO7.8. Release of $P_{tet}$-T11 promoter is possible as (5') Xho I/Sal I or Nco I (3') fragment.

II) Construction of Expression Plasmid and Transfection of Target Cells

The promoters T1 to T11 were directly introduced via Xho I and Nco I into the pUHC131-1 plasmid (Bonin 1994, Gene 141: 75-77). The reference plasmid for Ptet-1 was generated by introducing Ptet-1 into the pUHC131-1 plasmid containing the T2 promoter via Xho I and Sac II. The reference plasmid for Ptet-1 was generated by introducing Ptet-14 from the pTRE-Tight plasmid (Clontech Laboratories, Inc., US) into the pUHC131-1 plasmid containing the T4 promoter via Xho I and Sac I. The nucleotide sequence of all constructs was verified by sequencing.

EXAMPLE 2

Functional Analysis of the Transcription Control Sequences

The performance of the new promoter series was compared to the currently available tetracycline dependent promoters after transient transfection into HeLa M2 cells with (+) and without (−) doxycycline (Dox).

Hela cells stably expressing the reverse tetracycline dependent transactivator M2 were transiently transfected with 0.5 ug of a reporter construct (luciferase) under control of the various promoters under non-inducing conditions. Determination of unregulated activity (−Dox) showed that $P_{tet}$-T1 presented the highest background activity with a stepwise decrease in measurable activity from $P_{tet}$-T1 to $P_{tet}$-T6 (see FIG. 2).

For comparison of reporter activity in the induced and non-induced state, $P_{tet}$-T6, $P_{tet}$-T7, $P_{tet}$-14, $P_{tet}$-1 and a constitutively expressed reporter construct ($P_{hCMV}$) were analysed under the same conditions (FIG. 3). From these experiments it is clear that while reporter activity under inducing conditions (+Dox) reaches the same level after transfection of $P_{tet}$-T6, $P_{tet}$-T7, $P_{tet}$-14, which is about 2 fold increased compared with $Ph_{CMV}$, significant differences can be seen under non inducing conditions. Here transfection of $P_{tet}$-1 confers the highest activity which is about 1000 fold lower than activity of the $P_{hCMV}$ driven construct. Luciferase activity decreases stepwise from $P_{tet}$-T14, $P_{tet}$-T7, $P_{tet}$-6 which confers 100-fold lower background activity than $P_{tet}$-1 (Gossen 1992, loc. cit.).

Among the analyzed promoters, $P_{tet}$-T6 is the optimal tet-responsive promoter, in transient expression experiments its background activity is 100-fold lower than the activity of $P_{tet}$-1 (Gossen 1992, loc. cit.) and 10-fold lower than the activity conferred by $P_{tet}$-14 (commercially available from Clontech Laboratories, Inc. US).

EXAMPLE 3

Quantification of CpG-Ptet Variants

Hela-M2 cells were transfected under standard conditions via lipofection with the expression constructs recited in Table 3, below. Quantification of the expression was done by P/Rluc assay. In the Table, the activity of the indicated promoter constructs linked to firefly luciferase is shown, with a TK-Rluc (Renilla) internal control for standardisation. Rlu values given are for +dox conditions (induced). In no case the −dox values could be quantified as they were identical to background readings of the assay system. Minimal regulation factors were estimated assuming that the effective background was less than 10% of the instrument's blank readings.

In other (transient) experiments the activity of the CpG-free $P_{tet}$-T6$^{syn}$ was repeatedly 3-6 fold below that of the original T6, while the CpG-free bidirectional T6syn was always significantly more active.

TABLE 3

| | Expression in Hela-M2 cells | | | | | |
|---|---|---|---|---|---|---|
| | $P_{tet}$-T6 | | $P_{tet}$-T6$^{syn}$ | | $P_{tet}$-bi-T6$^{syn}$ | |
| Firefly luc (rlu, -bgd) | 436565 | 483755 | 98464 | 102316 | 2019532 | 2076652 |
| Renilla luc (rlu, -bgd) | 700 | 760 | 825 | 855 | 1218 | 1234 |
| Ratio Firefly/Renilla | 624 | 637 | 119 | 120 | 1219 | 1234 |
| Relative activity | 100 | | 19 | | 195 | |
| Regulation factor | >25.000 | | >5.000 | | >100.000 | |

EXAMPLE 4

Transient Transfection of MMTV-Based $P_{tet}$ Promoters in HEK293 Cells

MMTV-based $P_{tet}$ promoters were tested in HEK293 cells and compared with $P_{tet}$-14 from the pTRE-Tight plasmid (Clontech Laboratories, Inc., US) and the above described $P_{tet}$-T6. HEK293 cells were chosen since these cells have been described as being crucial with respect to background effects. Cultivation, transfection and activity measurement was carried out as described in Examples 2 or 3 for HeLa cells. HEK293 cells were transiently co-transfect with an rtTA expressing plasmid (Tet-O-Advanced, Clontech, USA). The results are shown in the following Table 4. It is evident that all MMTV-based $P_{tet}$ promoters show a significantly lower basal activity than the commercially available $P_{tet}$-14 promoter (tight). Moreover, the promoters even show a lower basal activity than the T6 promoter.

TABLE 4

Transient transfection of HEK293 cells

| promoter | HEK293, cotr. w/M2 vector | | |
|---|---|---|---|
| | no dox | dox | fold induction |
| $P_{tet}$-T8 | 0.51 | 45.5 | 89 |
| | 1 | 88.1 | 88 |
| $P_{tet}$-T9 | 0.43 | 19.9 | 46 |
| | 0.43 | 17.9 | 42 |
| $P_{tet}$-T10 | 0.6 | 62.1 | 104 |
| | 1.01 | 70 | 69 |

TABLE 4-continued

Transient transfection of HEK293 cells

| promoter | HEK293, cotr. w/M2 vector | | |
|---|---|---|---|
| | no dox | dox | fold induction |
| $P_{tet}$-T11 | 0.07 | 30.3 | 433 |
| | 0.23 | 31.3 | 136 |
| $P_{tet}$-T6 | 0.98 | 747 | 762 |
| | 0.72 | 499 | 693 |
| $P_{tet}$-14 (tight) | 2.01 | 424 | 211 |
| | 1.79 | 488 | 273 |

The invention claimed is:

1. A nucleic acid, wherein the nucleic acid has a sequence that is at least 90% identical to the sequence of any one of SEQ ID NO: 13, SEQ ID NO: 14, SEQ ID NO: 15, SEQ ID NO: 16, and SEQ ID NO: 17.

2. A vector comprising the nucleic acid of claim 1.

3. The vector of claim 2, wherein the vector is an expression vector.

4. The vector of claim 3, wherein the nucleic acid is operatively linked to a second nucleic acid sequence to be expressed.

5. A method for regulating the expression of a second nucleic acid sequence operatively linked to the nucleic acid of claim 1 in a host cell, in a non-human animal, or in a plant, the method comprising:
(a) providing a host cell, a non-human animal, or a plant comprising the second nucleic acid operatively linked to the nucleic acid of claim 1;
(b) expressing in the host cell, non-human animal, or plant a polynucleotide encoding a tetracycline-dependent transcriptional regulator; and
(c) modulating the concentration of a tetracycline or analog thereof in the host cell, non-human animal or plant, wherein expression of the second nucleic acid sequence is regulated.

6. The method of claim 5, wherein the tetracycline-dependent transcriptional regulator binds to a tet operator in the absence of tetracycline or an analog thereof.

7. The method of claim 6, wherein the tetracycline-dependent transcriptional regulator activates expression of the second nucleic acid sequence.

8. The method of claim 6, wherein the tetracycline-dependent transcriptional regulator inhibits expression of the second nucleic acid sequence.

9. The method of claim 5, wherein the tetracycline-dependent transcriptional regulator binds to a tet operator in the presence of tetracycline or an analog thereof.

10. The method of claim 9, wherein the tetracycline-dependent transcriptional regulator activates expression of the second nucleic acid sequence.

11. The method of claim 9, wherein the tetracycline-dependent transcriptional regulator inhibits expression of the second nucleic acid sequence.

12. The nucleic acid of claim 1, wherein the nucleic acid has a sequence that is at least 90% identical to the sequence of SEQ ID NO: 16.

* * * * *

SEQUENCE LISTING

<160> NUMBER OF SEQ ID NOS: 71

<210> SEQ ID NO 1
<211> LENGTH: 19
<212> TYPE: DNA
<213> ORGANISM: artificial
<220> FEATURE:
<223> OTHER INFORMATION: tet operator

<400> SEQUENCE: 1
tccctatcag tgatagaga                                              19

<210> SEQ ID NO 2
<211> LENGTH: 128
<212> TYPE: DNA
<213> ORGANISM: artificial
<220> FEATURE:
<223> OTHER INFORMATION: hCMV minimal promoter

<400> SEQUENCE: 2
ggtaggcgtg tacggtggga ggcctatata agcagagctc gtttagtgaa ccgtcagatc    60
gcctggagac gccatccacg ctgttttgac ctccatagaa gacaccggga ccgatccagc   120
ctccgcgg                                                           128

<210> SEQ ID NO 3
<211> LENGTH: 7
<212> TYPE: DNA
<213> ORGANISM: artificial
<220> FEATURE:
<223> OTHER INFORMATION: TFIIB binding site

<400> SEQUENCE: 3 gggcgcc                                                              7

<210> SEQ ID NO 4
<211> LENGTH: 7
<212> TYPE: DNA
<213> ORGANISM: artificial
<220> FEATURE:
<223> OTHER INFORMATION: TFIID binding site, TATA Box

<400> SEQUENCE: 4 tataaaa                                                              7

<210> SEQ ID NO 5
<211> LENGTH: 126
<212> TYPE: DNA
<213> ORGANISM: artificial
<220> FEATURE:

```
<223> OTHER INFORMATION: minimal promoter from Ptet-T2

<400> SEQUENCE: 5
ggtaggcgtg tacggtgggc gcctataaaa gcagagctcg tttagtgaac cgtcagatcg    60
cctggagacg ccatccacgc tgttttgacc tccatagaag acaccgggac cgatccagcc   120
tccgcg                                                              126

<210> SEQ ID NO 6
<211> LENGTH: 19
<212> TYPE: DNA
<213> ORGANISM: artificial
<220> FEATURE:
<223> OTHER INFORMATION: RFX-1 binding site

<400> SEQUENCE: 6
ccgtaaccac ttgcaaccc                                                 19

<210> SEQ ID NO 7
<211> LENGTH: 10
<212> TYPE: DNA
<213> ORGANISM: artificial
<220> FEATURE:
<223> OTHER INFORMATION: AP4 binding site

<400> SEQUENCE: 7
tccagctctc                                                           10

<210> SEQ ID NO 8
<211> LENGTH: 20
<212> TYPE: DNA
<213> ORGANISM: artificial
<220> FEATURE:
<223> OTHER INFORMATION: HP-1 binding site

<400> SEQUENCE: 8
cagctctctt ttgacaactg                                                20

<210> SEQ ID NO 9
<211> LENGTH: 24
<212> TYPE: DNA
<213> ORGANISM: artificial
<220> FEATURE:
<223> OTHER INFORMATION: HP-2 binding site

<400> SEQUENCE: 9
caaccctcgt aagacaattg caaa                                           24

<210> SEQ ID NO 10
<211> LENGTH: 66
<212> TYPE: DNA
<213> ORGANISM: artificial
<220> FEATURE:
<223> OTHER INFORMATION: modified minimal promoter form Ptet-T4

<400> SEQUENCE: 10
taggcgtgta cggtgggcgc ctataaaagc agagctcgtt tagtgaaccg tcagatcgcc    60
tggaga                                                               66

<210> SEQ ID NO 11
<211> LENGTH: 89
<212> TYPE: DNA
<213> ORGANISM: artificial
<220> FEATURE:
<223> OTHER INFORMATION: TYMV 5 UTR
```

```
<400> SEQUENCE: 11
gtaatcaact accaattcca gctctctttt gacaactggt cttataccaa ctttccgtac      60
cacttgcaac cctcgtaaga caattgcaa                                        89

<210> SEQ ID NO 12
<211> LENGTH: 58
<212> TYPE: DNA
<213> ORGANISM: artificial
<220> FEATURE:
<223> OTHER INFORMATION: modified TYMV 5 UTR from Ptet-T6

<400> SEQUENCE: 12
aattccacaa cacttttgtc ttataccaac tttccgtacc acttcctacc ctcgtaaa       58

<210> SEQ ID NO 13
<211> LENGTH: 345
<212> TYPE: DNA
<213> ORGANISM: artificial
<220> FEATURE:
<223> OTHER INFORMATION: Ptet-T3

<400> SEQUENCE: 13
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
tttactccct atcagtgata gagaacgtat atccagttta ctccctatca gtgatagaga     240
acgtataagc tttaggcgtg tacggtgggc gcctataaaa gcagagctcg tttagtgaac     300
cgtcagatcg cctggagacg ccatccacgc tgtttccata gaaga                     345

<210> SEQ ID NO 14
<211> LENGTH: 318
<212> TYPE: DNA
<213> ORGANISM: artificial
<220> FEATURE:
<223> OTHER INFORMATION: Ptet-T4

<400> SEQUENCE: 14
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
tttactccct atcagtgata gagaacgtat atccagttta ctccctatca gtgatagaga     240
acgtataagc tttaggcgtg tacggtgggc gcctataaaa gcagagctcg tttagtgaac     300
cgtcagatcg cctggaga                                                   318

<210> SEQ ID NO 15
<211> LENGTH: 406
<212> TYPE: DNA
<213> ORGANISM: artificial
<220> FEATURE:
<223> OTHER INFORMATION: Ptet-T5

<400> SEQUENCE: 15
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
```

```
tttactccct atcagtgata gagaacgtat atccagttta ctccctatca gtgatagaga    240
acgtataagc tttaggcgtg tacggtgggc gcctataaaa gcagagctcg tttagtgaac    300
cgtcagatcg cctggaggta atcaactacc aattccagct ctcttttgac aactggtctt    360
ataccaactt tccgtaccac ttcctaccct cgtaagacaa ttgcaa                   406
```

<210> SEQ ID NO 16
<211> LENGTH: 376
<212> TYPE: DNA
<213> ORGANISM: artificial
<220> FEATURE:
<223> OTHER INFORMATION: Ptet-T6

<400> SEQUENCE: 16

```
tttactccct atcagtgata gagaacgtat gaagagttta ctccctatca gtgatagaga     60
acgtatgcag actttactcc ctatcagtga tagagaacgt ataaggagtt tactccctat    120
cagtgataga gaacgtatga ccagtttact ccctatcagt gatagagaac gtatctacag    180
tttactccct atcagtgata gagaacgtat atccagttta ctccctatca gtgatagaga    240
acgtataagc tttaggcgtg tacggtgggc gcctataaaa gcagagctcg tttagtgaac    300
cgtcagatcg cctggagcaa ttccacaaca cttttgtctt ataccaactt tccgtaccac    360
ttcctaccct cgtaaa                                                    376
```

<210> SEQ ID NO 17
<211> LENGTH: 407
<212> TYPE: DNA
<213> ORGANISM: artificial
<220> FEATURE:
<223> OTHER INFORMATION: Ptet-T7

<400> SEQUENCE: 17

```
tttactccct atcagtgata gagaacgtat gaagagttta ctccctatca gtgatagaga     60
acgtatgcag actttactcc ctatcagtga tagagaacgt ataaggagtt tactccctat    120
cagtgataga gaacgtatga ccagtttact ccctatcagt gatagagaac gtatctacag    180
tttactccct atcagtgata gagaacgtat atccagttta ctccctatca gtgatagaga    240
acgtataagc tttaggcgtg tacggtgggc gcctataaaa gcagagctcg tttagtgaac    300
cgtcagatcg cctggagcta atcaactacc aattccagct ctcttttgac aactggtctt    360
ataccaactt tccgtaccac ttcctaccct cctaagacaa ttgcaaa                  407
```

<210> SEQ ID NO 18
<211> LENGTH: 210
<212> TYPE: DNA
<213> ORGANISM: artificial
<220> FEATURE:
<223> OTHER INFORMATION: MMTV minimal promoter

<400> SEQUENCE: 18

```
gcctatgttc ttttggaatc tatccaagtc ttatgtaaat gcttatgtaa accataatat     60
aaaagagtgc tgattttttg agtaaacttg caacagtcct aacattcttc tctcgtgtgt    120
ttgtgtctgt tcgccatccc gtctccgctc gtcacttatc cttcactttt cagagggtcc    180
ccccgcagat cccggtcacc ctcaggtcgg                                     210
```

<210> SEQ ID NO 19
<211> LENGTH: 462
<212> TYPE: DNA
<213> ORGANISM: artificial

<220> FEATURE:
<223> OTHER INFORMATION: Ptet-T8

<400> SEQUENCE: 19

```
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
tttactccct atcagtgata gagaacgtat atccagttta ctccctatca gtgatagaga     240
acgtataagc ttgcctatgt tcttttggaa tctatccaag tcttatgtaa atgcttatgt     300
aaaccataat ataaaagagt gctgattttt tgagtaaact tgcaacagtc ctaacattct     360
tctctcgtgt gtttgtgtct gttcgccatc ccgtctccgc tcgtcactta tccttcactt     420
ttcagagggt cccccccgcag atcccggtca ccctcaggtc gg                       462
```

<210> SEQ ID NO 20
<211> LENGTH: 10
<212> TYPE: DNA
<213> ORGANISM: artificial
<220> FEATURE:
<223> OTHER INFORMATION: Oct-11 OTF-1 binding sites

<400> SEQUENCE: 20

```
atgtaaatct                                                             10
```

<210> SEQ ID NO 21
<211> LENGTH: 14
<212> TYPE: DNA
<213> ORGANISM: artificial
<220> FEATURE:
<223> OTHER INFORMATION: NF 1 binding site

<400> SEQUENCE: 21

```
tggaatctat ccaa                                                        14
```

<210> SEQ ID NO 22
<211> LENGTH: 12
<212> TYPE: DNA
<213> ORGANISM: artificial
<220> FEATURE:
<223> OTHER INFORMATION: FOX A1-1 binding site

<400> SEQUENCE: 22

```
atgtaaatgc tt                                                          12
```

<210> SEQ ID NO 23
<211> LENGTH: 411
<212> TYPE: DNA
<213> ORGANISM: artificial
<220> FEATURE:
<223> OTHER INFORMATION: Ptet-T9

<400> SEQUENCE: 23

```
tttactccct atcagtgata gagaacgtat gaagagttta ctccctatca gtgatagaga      60
acgtatgcag actttactcc ctatcagtga tagagaacgt ataaggagtt tactccctat     120
cagtgataga gaacgtatga ccagtttact ccctatcagt gatagagaac gtatctacag     180
tttactccct atcagtgata gagaacgtat atccagttta ctccctatca gtgatagaga     240
acgtataagc ttccataata taaaagagtg ctgattttt gagtaaactt gcaacagtcc      300
taacattctt ctctcgtgtg tttgtgtctg ttcgccatcc cgtctccgct cgtcacttat     360
``` ccttcactttt tcagagggtc cccccgcaga tcccggtcac cctcaggtcg g    411

<210> SEQ ID NO 24
<211> LENGTH: 415
<212> TYPE: DNA
<213> ORGANISM: artificial
<220> FEATURE:
<223> OTHER INFORMATION: Ptet-T10

<400> SEQUENCE: 24
tttactccct atcagtgata gagaacgtat gaagagttta ctccctatca gtgatagaga    60
acgtatgcag actttactcc ctatcagtga tagagaacgt ataaggagtt tactccctat    120
cagtgataga gaacgtatga ccagtttact ccctatcagt gatagagaac gtatctacag    180
tttactccct atcagtgata gagaacgtat atccagttta ctccctatca gtgatagaga    240
acgtataagc ttccagggcg cctataaaag agtgctgatt ttttgagtaa acttgcaaca    300
gtcctaacat tcttctctcg tgtgtttgtg tctgttcgcc atcccgtctc cgctcgtcac    360
ttatccttca cttttcagag ggtcccccccg cagatcccgg tcaccctcag gtcgg    415

<210> SEQ ID NO 25
<211> LENGTH: 365
<212> TYPE: DNA
<213> ORGANISM: artificial
<220> FEATURE:
<223> OTHER INFORMATION: Ptet-T11

<400> SEQUENCE: 25
tttactccct atcagtgata gagaacgtat gaagagttta ctccctatca gtgatagaga    60
acgtatgcag actttactcc ctatcagtga tagagaacgt ataaggagtt tactccctat    120
cagtgataga gaacgtatga ccagtttact ccctatcagt gatagagaac gtatctacag    180
tttactccct atcagtgata gagaacgtat atccagttta ctccctatca gtgatagaga    240
acgtataagc tttgcttatg taaaccaggg cgcctataaa agagtgctga ttttttgagt    300
aaacttcaat tccacaacac ttttgtctta taccaacttt ccgtaccact tcctaccctc    360
gtaaa    365

<210> SEQ ID NO 26
<211> LENGTH: 63
<212> TYPE: DNA
<213> ORGANISM: artificial
<220> FEATURE:
<223> OTHER INFORMATION: TOH-1 forward

<400> SEQUENCE: 26
tcgagtttac tccctatcag tgatagagaa cgtatgaaga gtttactccc tatcagtgat    60
aga    63

<210> SEQ ID NO 27
<211> LENGTH: 54
<212> TYPE: DNA
<213> ORGANISM: artificial
<220> FEATURE:
<223> OTHER INFORMATION: TOH-1 reverse

<400> SEQUENCE: 27
caaatgaggg atagtcacta tctcttgcat acttctcaaa tgagggatag tcac    54

<210> SEQ ID NO 28
<211> LENGTH: 59

```
<212> TYPE: DNA
<213> ORGANISM: artificial
<220> FEATURE:
<223> OTHER INFORMATION: TOH-2 forward

<400> SEQUENCE: 28
gaacgtatgc agactttact ccctatcagt gatagagaac gtataaggag tttactccc      59

<210> SEQ ID NO 29
<211> LENGTH: 59
<212> TYPE: DNA
<213> ORGANISM: artificial
<220> FEATURE:
<223> OTHER INFORMATION: TOH-2 reverse

<400> SEQUENCE: 29
tatctcttgc atacgtctga atgagggat agtcactatc tcttgcatat tcctcaaat       59

<210> SEQ ID NO 30
<211> LENGTH: 57
<212> TYPE: DNA
<213> ORGANISM: artificial
<220> FEATURE:
<223> OTHER INFORMATION: TOH-3 forward

<400> SEQUENCE: 30
tatcagtgat agagaacgta tgaccagttt actccctatc agtgatagag aacgtat       57

<210> SEQ ID NO 31
<211> LENGTH: 66
<212> TYPE: DNA
<213> ORGANISM: artificial
<220> FEATURE:
<223> OTHER INFORMATION: TOH-3 reverse

<400> SEQUENCE: 31
gagggatagt cactatctct tgcatactgg tcaaatgagg gatagtcact atctcttgca     60
tagatg                                                                66

<210> SEQ ID NO 32
<211> LENGTH: 62
<212> TYPE: DNA
<213> ORGANISM: artificial
<220> FEATURE:
<223> OTHER INFORMATION: TOH-4 forward

<400> SEQUENCE: 32
ctacagttta ctccctatca gtgatagaga acgtatatcc agtttactcc ctatcagtga     60
ta                                                                    62

<210> SEQ ID NO 33
<211> LENGTH: 62
<212> TYPE: DNA
<213> ORGANISM: artificial
<220> FEATURE:
<223> OTHER INFORMATION: TOH-4 reverse

<400> SEQUENCE: 33
ctacagttta ctccctatca gtgatagaga acgtatatcc agtttactcc ctatcagtga     60
ta                                                                    62

<210> SEQ ID NO 34
<211> LENGTH: 65
<212> TYPE: DNA
```

<213> ORGANISM: artificial
<220> FEATURE:
<223> OTHER INFORMATION: TOH-5 forward

<400> SEQUENCE: 34
gagaacgtat aagctttagg cgtgtacggt gggcgcctat aaaagcagag ctcgtttagt    60
gaacc    65

<210> SEQ ID NO 35
<211> LENGTH: 56
<212> TYPE: DNA
<213> ORGANISM: artificial
<220> FEATURE:
<223> OTHER INFORMATION: TOH-5 reverse

<400> SEQUENCE: 35
tgcatattcg aaatccgcac atgccacccg cggatatttt cgtctcgagc aaatca    56

<210> SEQ ID NO 36
<211> LENGTH: 58
<212> TYPE: DNA
<213> ORGANISM: artificial
<220> FEATURE:
<223> OTHER INFORMATION: TOH-6 forward

<400> SEQUENCE: 36
gtcagatcgc ctggagacgc catccacgct gttttgacct ccatagaaga gtcgacac    58

<210> SEQ ID NO 37
<211> LENGTH: 67
<212> TYPE: DNA
<213> ORGANISM: artificial
<220> FEATURE:
<223> OTHER INFORMATION: TOH-6 reverse

<400> SEQUENCE: 37
cttggcagtc tagcggacct ctgcggtagg tgcgacaaaa ctggaggtat cttctcagct    60
gtggtac    67

<210> SEQ ID NO 38
<211> LENGTH: 31
<212> TYPE: DNA
<213> ORGANISM: artificial
<220> FEATURE:
<223> OTHER INFORMATION: TO7.s

<400> SEQUENCE: 38
cctccataga agagtcgaca ccatggtgag c    31

<210> SEQ ID NO 39
<211> LENGTH: 35
<212> TYPE: DNA
<213> ORGANISM: artificial
<220> FEATURE:
<223> OTHER INFORMATION: TO7.as

<400> SEQUENCE: 39
aaacagcgtg gatggcgtct ccaggcgatc tgacg    35

<210> SEQ ID NO 40
<211> LENGTH: 79
<212> TYPE: DNA
<213> ORGANISM: artificial
<220> FEATURE:
<223> OTHER INFORMATION: TO7.1s -continued

<400> SEQUENCE: 40
agctttaggc gtgtacggtg ggcgcctata aaagcagagc tcgtttagtg aaccgtcaga    60
tcgcctggag agtcgacac                                                79

<210> SEQ ID NO 41
<211> LENGTH: 79
<212> TYPE: DNA
<213> ORGANISM: artificial
<220> FEATURE:
<223> OTHER INFORMATION: TO7.1as

<400> SEQUENCE: 41
catggtgtcg actctccagg cgatctgacg gttcactaaa cgagctctgc ttttataggc    60
gcccaccgta cacgcctaa                                                79

<210> SEQ ID NO 42
<211> LENGTH: 64
<212> TYPE: DNA
<213> ORGANISM: artificial
<220> FEATURE:
<223> OTHER INFORMATION: TO7.2s

<400> SEQUENCE: 42
ataccaactt ccgtaccac ttcctaccct cgtaagacaa ttgcaagtcg acaccatggt    60
gagc                                                               64

<210> SEQ ID NO 43
<211> LENGTH: 60
<212> TYPE: DNA
<213> ORGANISM: artificial
<220> FEATURE:
<223> OTHER INFORMATION: TO7.2as

<400> SEQUENCE: 43
aagaccagtt gtcaaaagag agctggaatt ggtagttgat tacctccagg cgatctgacg    60

<210> SEQ ID NO 44
<211> LENGTH: 47
<212> TYPE: DNA
<213> ORGANISM: artificial
<220> FEATURE:
<223> OTHER INFORMATION: TO7.3s

<400> SEQUENCE: 44
ctttccgtac cacttcctac cctcgtaaag tcgacaccat ggtgagc                  47

<210> SEQ ID NO 45
<211> LENGTH: 47
<212> TYPE: DNA
<213> ORGANISM: artificial
<220> FEATURE:
<223> OTHER INFORMATION: TO7.3as

<400> SEQUENCE: 45
ttggtataag acaaaagtgt tgtggaattg ctccaggcga tctgacg                  47

<210> SEQ ID NO 46
<211> LENGTH: 61
<212> TYPE: DNA
<213> ORGANISM: artificial
<220> FEATURE:
<223> OTHER INFORMATION: TO7.4s

```
<400> SEQUENCE: 46
caactttccg taccacttcc taccctccta agacaattgc aaagtcgaca ccatggtgag    60
c                                                                  61

<210> SEQ ID NO 47
<211> LENGTH: 64
<212> TYPE: DNA
<213> ORGANISM: artificial
<220> FEATURE:
<223> OTHER INFORMATION: TO7.4as

<400> SEQUENCE: 47
gtataagacc agttgtcaaa agagagctgg aattggtagt tgattagctc caggcgatct    60
gacg                                                                64

<210> SEQ ID NO 48
<211> LENGTH: 30
<212> TYPE: DNA
<213> ORGANISM: artificial
<220> FEATURE:
<223> OTHER INFORMATION: MMTV-5 (-89)

<400> SEQUENCE: 48
accgaagctt gcctatgttc ttttggaatc                                    30

<210> SEQ ID NO 49
<211> LENGTH: 45
<212> TYPE: DNA
<213> ORGANISM: artificial
<220> FEATURE:
<223> OTHER INFORMATION: MMTV-3 (+122)

<400> SEQUENCE: 49
cccggtcacc ctcaggtcgg gtcgacacca tggccagata tcccc                   45

<210> SEQ ID NO 50
<211> LENGTH: 31
<212> TYPE: DNA
<213> ORGANISM: artificial
<220> FEATURE:
<223> OTHER INFORMATION: MMTV-5 (-37)

<400> SEQUENCE: 50
accgaagctt ccataatata aaagagtgct g                                  31

<210> SEQ ID NO 51
<211> LENGTH: 45
<212> TYPE: DNA
<213> ORGANISM: artificial
<220> FEATURE:
<223> OTHER INFORMATION: MMTV-3 (+122)

<400> SEQUENCE: 51
cccggtcacc ctcaggtcgg gtcgacacca tggccagata tcccc                   45

<210> SEQ ID NO 52
<211> LENGTH: 42
<212> TYPE: DNA
<213> ORGANISM: artificial
<220> FEATURE:
<223> OTHER INFORMATION: TO7.7-s

<400> SEQUENCE: 52
atcaagcttc cagggcgcct ataaaagagt gctgattttt tg                      42
```

<210> SEQ ID NO 53
<211> LENGTH: 31
<212> TYPE: DNA
<213> ORGANISM: artificial
<220> FEATURE:
<223> OTHER INFORMATION: TO7.7-as

<400> SEQUENCE: 53
atccatggtg tcgacccgac ctgagggtga c        31

<210> SEQ ID NO 54
<211> LENGTH: 42
<212> TYPE: DNA
<213> ORGANISM: artificial
<220> FEATURE:
<223> OTHER INFORMATION: TO7.8-s1

<400> SEQUENCE: 54
atcaagcttt gcttatgtaa accagggcgc ctataaaaga gt        42

<210> SEQ ID NO 55
<211> LENGTH: 49
<212> TYPE: DNA
<213> ORGANISM: artificial
<220> FEATURE:
<223> OTHER INFORMATION: TO7.8-as1

<400> SEQUENCE: 55
gtggaattga agtttactca aaaaatcagc actcttttat aggcgccct        49

<210> SEQ ID NO 56
<211> LENGTH: 52
<212> TYPE: DNA
<213> ORGANISM: artificial
<220> FEATURE:
<223> OTHER INFORMATION: TO7.8-s2

<400> SEQUENCE: 56
tgagtaaact tcaattccac aacactttg tcttatacca actttccgta cc        52

<210> SEQ ID NO 57
<211> LENGTH: 52
<212> TYPE: DNA
<213> ORGANISM: artificial
<220> FEATURE:
<223> OTHER INFORMATION: TO7.8-as2

<400> SEQUENCE: 57
atccatggtg tcgactttac gagggtagga agtggtacgg aaagttggta ta        52

<210> SEQ ID NO 58
<211> LENGTH: 146
<212> TYPE: DNA
<213> ORGANISM: artificial
<220> FEATURE:
<223> OTHER INFORMATION: sequence fragment of T1

<400> SEQUENCE: 58
aagcttggta ggcgtgtacg gtgggaggcc tatataagca gagctcgttt agtgaaccgt        60
cagatcgcct ggagacgcca tccacgctgt tttgacctcc atagaagaca ccgggaccga       120
tccagcctcc gcggtcgaca ccatgg       146

<210> SEQ ID NO 59

```
<211> LENGTH: 145
<212> TYPE: DNA
<213> ORGANISM: artificial
<220> FEATURE:
<223> OTHER INFORMATION: sequence fragment of T2

<400> SEQUENCE: 59
aagcttggta ggcgtgtacg gtgggcgcct ataaaagcag agctcgttta gtgaaccgtc      60
agatcgcctg gagacgccat ccacgctgtt ttgacctcca tagaagacac cgggaccgat     120
ccagcctccg cggtcgacac catgg                                            145

<210> SEQ ID NO 60
<211> LENGTH: 112
<212> TYPE: DNA
<213> ORGANISM: artificial
<220> FEATURE:
<223> OTHER INFORMATION: sequence fragment of T3

<400> SEQUENCE: 60
aagctttagg cgtgtacggt gggcgcctat aaaagcagag ctcgtttagt gaaccgtcag      60
atcgcctgga gacgccatcc acgctgtttc catagaagag tcgacaccat gg             112

<210> SEQ ID NO 61
<211> LENGTH: 85
<212> TYPE: DNA
<213> ORGANISM: artificial
<220> FEATURE:
<223> OTHER INFORMATION: sequence fragment of T4

<400> SEQUENCE: 61
aagctttagg cgtgtacggt gggcgcctat aaaagcagag ctcgtttagt gaaccgtcag      60
atcgcctgga gagtcgacac catgg                                            85

<210> SEQ ID NO 62
<211> LENGTH: 173
<212> TYPE: DNA
<213> ORGANISM: artificial
<220> FEATURE:
<223> OTHER INFORMATION: sequence fragment of T5

<400> SEQUENCE: 62
aagctttagg cgtgtacggt gggcgcctat aaaagcagag ctcgtttagt gaaccgtcag      60
atcgcctgga ggtaatcaac taccaattcc agctctcttt tgacaactgg tcttatacca    120
actttccgta ccacttccta ccctcgtaag acaattgcaa gtcgacacca tgg            173

<210> SEQ ID NO 63
<211> LENGTH: 142
<212> TYPE: DNA
<213> ORGANISM: artificial
<220> FEATURE:
<223> OTHER INFORMATION: sequence fragment of T6

<400> SEQUENCE: 63
aagctttagg cgtgtacggt gggcgcctat aaaagcagag ctcgtttagt gaaccgtcag      60
atcgcctgga gaattccaca acactttgt cttataccaa ctttccgtac cacttcctac     120
cctcgtaaag tcgacaccat gg                                              142

<210> SEQ ID NO 64
<211> LENGTH: 174
<212> TYPE: DNA
<213> ORGANISM: artificial
```

```
<220> FEATURE:
<223> OTHER INFORMATION: sequence fragment of T7

<400> SEQUENCE: 64
aagctttagg cgtgtacggt gggcgcctat aaaagcagag ctcgtttagt gaaccgtcag      60
atcgcctgga gctaatcaac taccaattcc agctctcttt tgacaactgg tcttatacca    120
actttccgta ccacttccta ccctcctaag acaattgcaa agtcgacacc atgg          174

<210> SEQ ID NO 65
<211> LENGTH: 262
<212> TYPE: DNA
<213> ORGANISM: artificial
<220> FEATURE:
<223> OTHER INFORMATION: fragment 1 of Ptet-T6syn

<400> SEQUENCE: 65
gaattcttta ctccctatca gtgatagaga atgtatgaag agtttactcc ctatcagtga     60
tagagaatgt atgcagactt tactccctat cagtgataga gaatgtataa ggagtttact   120
ccctatcagt gatagagaat gtatgaccag tttactccct atcagtgata gagaatgtat   180
ctacagttta ctccctatca gtgatagaga atgtatatcc agtttactcc ctatcagtga   240
tagagaatgt ataagcttta gg                                             262

<210> SEQ ID NO 66
<211> LENGTH: 133
<212> TYPE: DNA
<213> ORGANISM: artificial
<220> FEATURE:
<223> OTHER INFORMATION: fragment 2 of Ptet-T6syn

<400> SEQUENCE: 66
catgtacagt gggcacctat aaaagcagag ctcatttagt gaactgtcag attgcctgga     60
gcaattccac aacactttg tcttatacca actttccata ccacttccta ccctcataaa   120
gtgcacacca tgg                                                       133

<210> SEQ ID NO 67
<211> LENGTH: 150
<212> TYPE: DNA
<213> ORGANISM: artificial
<220> FEATURE:
<223> OTHER INFORMATION: fragment 1 of bidirectional Ptet-T6

<400> SEQUENCE: 67
ccatggtgtg cactttatga gggtaggaag tggtatggaa agttggtata agacaaaagt     60
gttgtggaat tgctccaggc aatctgacag ttcactaaat gagctctgct tttataggtg   120
cccactgtac atgcctaaga attctttact                                     150

<210> SEQ ID NO 68
<211> LENGTH: 250
<212> TYPE: DNA
<213> ORGANISM: artificial
<220> FEATURE:
<223> OTHER INFORMATION: fragment 2 of bidirectional Ptet-T6

<400> SEQUENCE: 68
ccctatcagt gatagagaat gtatgaagag tttactccct atcagtgata gagaatgtat     60
gcagacttta ctccctatca gtgatagaga atgtataagg agtttactcc ctatcagtga   120
tagagaatgt atgaccagtt tactccctat cagtgataga gaatgtatct acagtttact   180
```

```
ccctatcagt gatagagaat gtatatccag tttactccct atcagtgata gagaatgtat    240
aagctttagg                                                           250

<210> SEQ ID NO 69
<211> LENGTH: 133
<212> TYPE: DNA
<213> ORGANISM: artificial
<220> FEATURE:
<223> OTHER INFORMATION: fragment 3 of bidirectional Ptet-T6

<400> SEQUENCE: 69
catgtacagt gggcacctat aaaagcagag ctcatttagt gaactgtcag attgcctgga     60
gcaattccac aacacttttg tcttatacca actttccata ccacttccta ccctcataaa    120
gtgcacacca tgg                                                      133

<210> SEQ ID NO 70
<211> LENGTH: 8
<212> TYPE: DNA
<213> ORGANISM: artificial
<220> FEATURE:
<223> OTHER INFORMATION: Oct12 (OTF-1) binding sites

<400> SEQUENCE: 70 atgtaaac                                                              8

<210> SEQ ID NO 71
<211> LENGTH: 11
<212> TYPE: DNA
<213> ORGANISM: artificial
<220> FEATURE:
<223> OTHER INFORMATION: FOX A1-2 binding site

<400> SEQUENCE: 71
atgtaaacca t                                                         11
```